(12) United States Patent
Trieu et al.

(10) Patent No.: US 9,763,892 B2
(45) Date of Patent: Sep. 19, 2017

(54) IMMEDIATE RELEASE PHOSPHOLIPID-COATED THERAPEUTIC AGENT NANOPARTICLES AND RELATED METHODS

(71) Applicant: Autotelic LLC, City of Industry, CA (US)

(72) Inventors: Vuong Trieu, Agoura Hills, CA (US); Tapas K. De, Culver City, CA (US)

(73) Assignee: Autotelic LLC, City of Industry, CA (US)

(*) Notice: Subject to any disclaimer, the term of this patent is extended or adjusted under 35 U.S.C. 154(b) by 0 days.

(21) Appl. No.: 15/208,307

(22) Filed: Jul. 12, 2016

(65) Prior Publication Data

US 2016/0346220 A1    Dec. 1, 2016

Related U.S. Application Data

(63) Continuation of application No. PCT/US2016/035293, filed on Jun. 1, 2016.

(60) Provisional application No. 62/169,397, filed on Jun. 1, 2015, provisional application No. 62/263,453, filed on Dec. 4, 2015, provisional application No. 62/323,335, filed on Apr. 15, 2016.

(51) Int. Cl.
| A61K 9/107 | (2006.01) |
| A61K 9/51 | (2006.01) |
| A61K 31/337 | (2006.01) |
| A61K 9/16 | (2006.01) |
| A61K 9/50 | (2006.01) |
| A61K 9/00 | (2006.01) |

(52) U.S. Cl.
CPC .......... *A61K 9/5123* (2013.01); *A61K 9/0019* (2013.01); *A61K 9/1075* (2013.01); *A61K 9/1617* (2013.01); *A61K 9/5084* (2013.01); *A61K 9/5192* (2013.01); *A61K 31/337* (2013.01)

(58) Field of Classification Search
CPC .. A61K 9/1617; A61K 9/5084; A61K 9/5192; A61K 47/48869; A61K 47/4869
See application file for complete search history.

(56) References Cited

U.S. PATENT DOCUMENTS

| 4,868,158 | A | 9/1989 | Masquelier et al. |
| 5,128,318 | A | 7/1992 | Levine et al. |
| 5,284,831 | A | 2/1994 | Kahl et al. |
| 5,324,821 | A | 6/1994 | Favre et al. |
| 5,576,016 | A | 11/1996 | Amselem et al. |

(Continued)

FOREIGN PATENT DOCUMENTS

| WO | 98/13385 A2 | 4/1998 |
| WO | 98/46275 A2 | 10/1998 |

(Continued)

OTHER PUBLICATIONS

Krishnamurthy et al, "Lipid-coated polymeric nanoparticlle for cancer drug delivery", Biomater. Sci, 2015, 3, 923-936.*

(Continued)

*Primary Examiner* — Carlos Azpuru
(74) *Attorney, Agent, or Firm* — Christensen O'Connor Johnson Kindness

(57) ABSTRACT

Phospholipid-coated nanoparticles containing a therapeutic agent, compositions that include the nanoparticles, and methods for making and using the nanoparticles and compositions.

30 Claims, 14 Drawing Sheets

(56) References Cited

U.S. PATENT DOCUMENTS

| | | | |
|---|---|---|---|
| 5,637,625 A | 6/1997 | Haynes | |
| 5,652,339 A | 7/1997 | Lerch et al. | |
| 5,795,587 A | 8/1998 | Gao et al. | |
| 5,874,059 A | 2/1999 | Maranhão | |
| 5,916,596 A | 6/1999 | Desai et al. | |
| 5,922,754 A | 7/1999 | Burchett et al. | |
| 5,981,501 A | 11/1999 | Wheeler et al. | |
| 6,096,331 A | 8/2000 | Desai et al. | |
| 6,287,590 B1 | 9/2001 | Dasseux | |
| 6,294,192 B1 | 9/2001 | Patel et al. | |
| 6,322,805 B1 | 11/2001 | Kim et al. | |
| 6,335,029 B1 | 1/2002 | Kamath et al. | |
| 6,506,405 B1 | 1/2003 | Desai et al. | |
| 6,514,523 B1 | 2/2003 | Sparks | |
| 6,545,097 B2 | 4/2003 | Pinchuk et al. | |
| 6,589,546 B2 | 7/2003 | Kamath et al. | |
| 6,726,925 B1 | 4/2004 | Needham | |
| 6,855,770 B2 | 2/2005 | Pinchuk et al. | |
| 6,923,988 B2 | 8/2005 | Patel et al. | |
| 6,939,320 B2 | 9/2005 | Lennox | |
| 7,053,049 B2 | 5/2006 | Luescher et al. | |
| 7,179,484 B2 | 2/2007 | Singh | |
| 7,220,833 B2 | 5/2007 | Nelson et al. | |
| 7,387,623 B2 | 6/2008 | MacLeod | |
| RE40,493 E | 9/2008 | Straub et al. | |
| 7,655,038 B2 | 2/2010 | Luthra et al. | |
| 7,771,468 B2 | 8/2010 | Whitbourne et al. | |
| 7,820,788 B2 | 10/2010 | Desai et al. | |
| 7,879,360 B2 | 2/2011 | Cunningham et al. | |
| 7,881,808 B2 | 2/2011 | Borgaonkar et al. | |
| 7,923,536 B2 | 4/2011 | Desai et al. | |
| 7,981,445 B2 | 7/2011 | De et al. | |
| 8,034,765 B2 | 10/2011 | De et al. | |
| 8,043,361 B2 | 10/2011 | Dicarlo et al. | |
| 8,101,200 B2 | 1/2012 | Whitbourne et al. | |
| 8,137,684 B2 | 3/2012 | Desai et al. | |
| 8,138,229 B2 | 3/2012 | Desai et al. | |
| 8,262,613 B2 | 9/2012 | Lennox | |
| 8,287,590 B2 | 10/2012 | Whitbourne et al. | |
| 8,293,277 B2 | 10/2012 | Swanson et al. | |
| 8,314,156 B2 | 11/2012 | Desai et al. | |
| 8,361,490 B2 | 1/2013 | Holzer et al. | |
| 8,454,945 B2 | 6/2013 | McCook et al. | |
| 8,475,822 B2 | 7/2013 | Hauenstein | |
| 8,552,056 B2 | 10/2013 | McChesney et al. | |
| 8,574,191 B2 | 11/2013 | Lennox | |
| 8,586,062 B2 | 11/2013 | Khopade et al. | |
| 8,603,531 B2 | 12/2013 | Yu et al. | |
| 8,668,919 B2 | 3/2014 | Ludwig et al. | |
| 8,845,716 B2 | 9/2014 | Lee et al. | |
| 8,846,771 B2 | 9/2014 | Desai et al. | |
| 8,853,260 B2 | 10/2014 | Desai et al. | |
| 8,911,786 B2 | 12/2014 | Desai et al. | |
| 8,980,300 B2 | 3/2015 | Pacetti et al. | |
| RE45,500 E | 4/2015 | Luthra et al. | |
| 9,005,161 B2 | 4/2015 | Wang | |
| 9,011,411 B2 | 4/2015 | Holzer et al. | |
| 9,012,518 B2 | 4/2015 | Desai et al. | |
| 9,012,519 B2 | 4/2015 | Desai et al. | |
| 9,018,246 B2 | 4/2015 | Ye et al. | |
| 2002/0012680 A1 | 1/2002 | Patel et al. | |
| 2002/0119198 A1 | 8/2002 | Gao et al. | |
| 2003/0008014 A1 | 1/2003 | Shelness | |
| 2003/0008015 A1 | 1/2003 | Levisage et al. | |
| 2003/0215496 A1 | 11/2003 | Patel et al. | |
| 2004/0022862 A1 | 2/2004 | Kipp et al. | |
| 2004/0033267 A1 | 2/2004 | Merisko-Liversidge et al. | |
| 2004/0076679 A1 | 4/2004 | Jones et al. | |
| 2004/0092577 A1 | 5/2004 | Lerner et al. | |
| 2004/0131646 A1 | 7/2004 | Trager et al. | |
| 2004/0234588 A1 | 11/2004 | Lu et al. | |
| 2004/0266662 A1 | 12/2004 | Rye et al. | |
| 2005/0191359 A1 | 9/2005 | Goldshtein et al. | |
| 2005/0238725 A1 | 10/2005 | Cunningham et al. | |
| 2006/0078619 A1 | 4/2006 | Woo et al. | |
| 2008/0050461 A1 | 2/2008 | Merisko-Liversidge et al. | |
| 2008/0138394 A1 | 6/2008 | Kim et al. | |
| 2008/0279949 A1 | 11/2008 | Merisko-Liversidge et al. | |
| 2008/0305173 A1 | 12/2008 | Bogue | |
| 2009/0087460 A1 | 4/2009 | Takebe et al. | |
| 2009/0110739 A1 | 4/2009 | Lacko et al. | |
| 2009/0215882 A1 | 8/2009 | Bouzada et al. | |
| 2010/0003332 A1 | 1/2010 | Bae et al. | |
| 2010/0267817 A1 | 10/2010 | Jang et al. | |
| 2010/0290983 A1 | 11/2010 | Rabinow et al. | |
| 2010/0297244 A1 | 11/2010 | Khopade et al. | |
| 2010/0305202 A1 | 12/2010 | Hwang et al. | |
| 2010/0329976 A1 | 12/2010 | Merisko-Liversidge et al. | |
| 2011/0200665 A1 | 8/2011 | Mei et al. | |
| 2011/0212169 A1 | 9/2011 | Bae et al. | |
| 2011/0306564 A1 | 12/2011 | Takebe et al. | |
| 2012/0087984 A1 | 4/2012 | Liversidge et al. | |
| 2013/0045222 A1 | 2/2013 | Hartikka et al. | |
| 2013/0195988 A1 | 8/2013 | Duan et al. | |
| 2013/0344116 A1 | 12/2013 | Wong et al. | |
| 2014/0023699 A1 | 1/2014 | McChesney et al. | |
| 2014/0030352 A1 | 1/2014 | Khopade et al. | |
| 2014/0066495 A1 | 3/2014 | Ye et al. | |
| 2014/0314664 A1 | 10/2014 | Qin et al. | |
| 2014/0363514 A1 | 12/2014 | Koyakutty et al. | |
| 2015/0030686 A1 | 1/2015 | Nitsche et al. | |
| 2015/0080353 A1 | 3/2015 | Singh et al. | |
| 2015/0209300 A1 | 7/2015 | Holzer et al. | |

FOREIGN PATENT DOCUMENTS

| | | |
|---|---|---|
| WO | 99/04761 A1 | 2/1999 |
| WO | 01/13939 A1 | 3/2001 |
| WO | 03/029294 A1 | 4/2003 |
| WO | 2005/039534 A1 | 5/2005 |
| WO | 2006/073419 A2 | 7/2006 |
| WO | 2006/100567 A1 | 9/2006 |
| WO | 2014/165672 A1 | 10/2014 |
| WO | 2014/165842 A2 | 10/2014 |
| WO | 2014/168845 A1 | 10/2014 |
| WO | 2014165829 A2 | 10/2014 |
| WO | 2015/042234 A1 | 3/2015 |

OTHER PUBLICATIONS

Office Action mailed Nov. 17, 2016, from U.S. Appl. No. 15/208,258, filed Jul. 12, 2016.

Riaz, M., "Liposomes Preparation Methods," Pakistan Journal of Pharmaceutical Sciences 19(1):65-77, Jan. 1996.

Talsma, H., et al., "The Size Reduction of Liposomes With a High Pressure Homogenizer (Microfluidizer™), Characterization of Prepared Dispersions and Comparison With Conventional Methods," Drug Development and Industrial Pharmacy 15(2):197-207, Jan. 1989.

Wang, R., et al., "Calculating Partition Coefficient by Atom-Additive Method," Perspectives in Drug Discovery and Design 19(1):47-66, Sep. 2000.

Wang, R., et al., "A New Atom-Additive Method for Calculating Partition Coefficients," Journal of Chemical Information and Computer Sciences, 37(3):615-621, May 1997.

International Search Report and Written Opinion mailed Aug. 26, 2016, issued in International Application No. PCT/US2016/035293, filed Jun. 1, 2016, 12 pages.

Office Action mailed Oct. 19, 2016, from U.S. Appl. No. 15/208,346, filed Jul. 12, 2016.

Yadav, D.K., et al., "Development of Novel Docetaxel Phospholipid Nanoparticles for Intravenous Administration: Quality by Design Approach," AAPS PharmSciTech 16(4):855-864, Aug. 2015.

\* cited by examiner

Table 4

| Method of Preparation | Phospholipid Constituents | | | | Size @ t=0 | % Paclitaxel Inc |
|---|---|---|---|---|---|---|
| | PC | | Lyso PC | | | |
| | Name | mg | Name | mg | | |
| Microfluidization Method 1 | PC 8 | 40 | Lyso 8 | 10 | 60 | Not detected |
| | PC 10 | 40 | Lyso 10 | 10 | 113 | 7 |
| | PC 8 | 40 | Lyso 12 | 10 | 79 | 0 |
| | PC 12 | 40 | Lyso 8 | 10 | 88 | 6 |
| | PC 12 | 40 | Lyso 12 | 10 | 95 | 45 |
| | PC 12 | 40 | Lyso 20 | 10 | 101.6 | 14.72 |
| | PC 12 | 50 | - | - | 129.2 | 4.57 |
| | Lyso 20 | 50 | - | - | 406.5 | 5.1 |
| | Lyso 12 | 50 | - | - | 108.2 | 23.6 |
| | PC 20 | 40 | Lyso 12 | 10 | 121.6 | Not detected |
| | PC 20 | 40 | Lyso 20 | 10 | 269.8 | Not detected |
| | PC 12 | 10 | Lyso 12 | 40 | 12.7 | 28.63 |
| | PC 12 | 10 | Lyso 20 | 40 | 213.2 | 21.26 |
| | PC 18:1 | 10 | Lyso 12 | 40 | 97.45 | 3.01 |
| | PC 18:1 | 10 | Lyso 20 | 40 | 443.3 | 15.15 |
| Thin Film Evaporation Method 2 | PC 8 | 40 | Lyso 8 | 10 | 396 | 0 |
| | PC 10 | 40 | Lyso 10 | 10 | 146 | 71 |
| | PC 8 | 40 | Lyso 12 | 10 | 22 | 1 |
| | PC 12 | 40 | Lyso 8 | 10 | 174 | 38 |
| | PC 12 | 40 | Lyso 12 | 10 | 139 | 63 |
| | PC 12 | 40 | Lyso 20 | 10 | 93.97 | 41.63 |
| | PC 12 | 50 | - | - | 540.4 | Not detected |
| | Lyso 20 | 50 | - | - | 738.36 | 4.1 |
| | Lyso 12 | 50 | - | - | 5.9 | 11.8 |
| | PC 20 | 40 | Lyso 12 | 10 | 22.96 | 4.32 |
| | PC 20 | 40 | Lyso 20 | 10 | 146.7 | 0.41 |
| | PC 12 | 10 | Lyso 12 | 40 | 8.726 | 2.56 |
| | PC 12 | 10 | Lyso 20 | 40 | 48.82 | 19.19 |
| | PC 18:1 | 10 | Lyso 12 | 40 | 10.37 | 1.95 |
| | PC 18:1 | 10 | Lyso 20 | 40 | 71.95 | 23.83 |

*FIG. 7*

IMMEDIATE RELEASE PHOSPHOLIPID-COATED THERAPEUTIC AGENT NANOPARTICLES AND RELATED METHODS

CROSS-REFERENCES TO RELATED APPLICATIONS

This application is a continuation of PCT/US2016/035293, filed Jun. 1, 2016, which claims priority to U.S. Application No. 62/169,397, filed Jun. 1, 2015, U.S. Application No. 62/263,453, filed Dec. 4, 2015, and U.S. Application No. 62/323,335, filed Apr. 15, 2016, each expressly incorporated herein by reference in its entirety.

BACKGROUND OF THE INVENTION

The effective delivery of hydrophobic therapeutic agents remains a challenging problem for the pharmaceutical industry. These challenges relate to the difficulty in formulating these therapeutic agents in vehicles for administration. Historically, hydrophobic therapeutic agents are administered in delivery vehicles that are less than advantageous with regard to delivery properties including therapeutic agent dose and bioavailability. Furthermore, serious side effects are occasionally observed associated with the vehicle itself.

The formulation of paclitaxel over the years is an example of the challenges associated with many hydrophobic therapeutic agents.

Paclitaxel is one of the most effective chemotherapeutic drugs and is used to treat mainly breast, lung and ovarian cancers. Taxol® is a paclitaxel formulation that utilizes a solvent, cremophor EL, to solubilize and deliver the essentially water-insoluble paclitaxel. Disadvantages and side effects of Taxol® are directly associated this solvent.

Paclitaxel has also been formulated as nanoparticles. Abraxane® is a nanoparticle paclitaxel formulation having improved paclitaxel solubility (0.35-0.7 µg/mL) compared to Taxol® and avoids the use of a harmful solvent. Abraxane® is a human serum albumin-coated paclitaxel nanoparticle. Cynviloq®, a polymeric micelle paclitaxel formulation that uses a biocompatible chemical polymer rather that a biological polymer to stabilize the nanoparticle, is a next-generation paclitaxel product.

Despite the advances in the development of alternative formulations that overcome the disadvantages associated with known hydrophobic therapeutic agent formulations, a need exists for new formulations of hydrophobic therapeutic agents having improved properties. The present invention seeks to fulfill these needs and provides further related advantages.

SUMMARY OF THE INVENTION

The present invention provides phospholipid-coated therapeutic agent nanoparticles suitable for administration by injection, pharmaceutical compositions that include the nanoparticle, methods for treating diseases and conditions treatable by the therapeutic agents, and methods for making the nanoparticles.

In one aspect, the invention provides phospholipid-coated therapeutic agent nanoparticle.

In one embodiment, the phospholipid-coated therapeutic agent nanoparticle, comprises a particulate therapeutic agent coated with one or more phospholipids, wherein the nanoparticle is stable in aqueous delivery vehicles for administration and releases the therapeutic agent substantially instantaneously upon exposure to physiological fluid.

In another embodiment, the phospholipid-coated therapeutic agent nanoparticle comprises a particulate therapeutic agent coated with one or more phospholipids, wherein the nanoparticle is as stable in aqueous delivery vehicles for administration as synthetic polymeric micelles containing a therapeutic agent (Genexol-PM®, Cynviloq®) and is as effective in releasing the therapeutic agent under physiological conditions as a human-serum albumin-coated therapeutic agent (Abraxane®).

In a further embodiment, the phospholipid-coated therapeutic agent nanoparticle comprises a particulate therapeutic agent coated with one or more phospholipids, wherein the phospholipid is a mono-acylphospholipid.

In another embodiment, the phospholipid-coated therapeutic agent nanoparticle comprises a particulate therapeutic agent coated with one or more phospholipids, wherein the phospholipid comprises a mono-acylphospholipid and a diacylphospholipid.

In a further embodiment, the phospholipid-coated therapeutic agent nanoparticle comprises a particulate therapeutic agent coated with one or more phospholipids, wherein the phospholipid is a diacylphospholipid having a fatty acid component having from 10 to 16 carbon atoms.

In another embodiment, the phospholipid-coated therapeutic agent nanoparticle comprises a particulate therapeutic agent coated with one or more phospholipids, wherein the nanoparticle is substantially electronically neutral based on phospholipid composition.

In a further embodiment, the phospholipid-coated therapeutic agent nanoparticle consists essentially of a particulate therapeutic agent coated with one or more phospholipids.

In another embodiment, the phospholipid-coated therapeutic agent nanoparticle consisting of a particulate therapeutic agent coated with one or more phospholipids.

In certain embodiments of the nanoparticle of the invention, the phospholipid is a diacylphospholipid. Suitable diacylphospholipids include diacylphosphatidylcholines, diacylphosphatidylethanolamines, diacylphosphatidylglycerols, diacylphosphatidylserines, diacylphosphatidylinositols, and diacylphosphatidic acids, and mixtures thereof. In certain embodiments, the phospholipid is a phosphatidylcholine. In certain embodiments, the phospholipid is a phosphatidylcholine having a fatty acid component having from 10 to 22 carbons. In other embodiments, the phospholipid is a phosphatidylcholine having a fatty acid component having from 10 to 12 carbons.

In certain embodiments of the nanoparticle of the invention, the phospholipid is a mono-acylphospholipid. Suitable mono-acylphospholipids include lysophosphatidylcholines, lysophosphatidylethanolamines, lysophosphatidylglycerols, lysophosphatidylserines, lysophosphatidylinositols, and lysophosphatidic acids, and mixtures thereof. In certain embodiments, the phospholipid is a lysophosphatidylcholine. In certain embodiments, the lysophosphatidylcholine having a fatty acid component having from 10 to 22 carbons. In other embodiments, the phospholipid is a lysophosphatidylcholine having a fatty acid component having from 10 to 12 carbons.

In certain embodiments of the nanoparticle of the invention, the phospholipid is a combination of a diacylphospholipid and a mono-acylphospholipid. In certain embodiments, the phospholipid is a combination of a phosphatidylcholine and a lysophosphatidylcholine. In certain embodiments that include a combination of a diacylphospholipid and a mono-acylphospholipid, the ratio of diacylphospholipid to mono-acylphospholipid is from about 90:10 to about 60:40 weight/ weight (w/w) percent. In other embodiments, the ratio of diacylphospholipid to mono-acylphospholipid of is about 80:20 w/w percent.

In certain embodiments, the nanoparticle includes a therapeutic agent having an X log P greater than 2.0.

Suitable therapeutic agents include analgesics/antipyretics, anesthetics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antianginal agents, antipsychotic agents, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines/antipruritics, agents useful for calcium regulation, antibacterial agents, antiviral agents, antimicrobials, anti-infectives, bronchodilators, hormones, hypoglycemic agents, hypolipidemic agents, proteins, nucleic acids, agents useful for erythropoiesis stimulation, antiulcer/antireflux agents, antinauseants/antiemetics, and oil-soluble vitamins. In certain embodiments, the therapeutic agent is a chemotherapeutic agent. Representative chemotherapeutic agents include taxanes, such as paclitaxel and derivatives thereof, and docetaxel and derivatives thereof. In certain embodiments, the therapeutic agent is paclitaxel.

In certain embodiments, the therapeutic agent is in crystalline form. In other embodiments, the therapeutic agent is in amorphous form.

In certain embodiments, the nanoparticle has an average diameter from about 30-300 nm. In other embodiments, the nanoparticle has an average diameter from about 80-200 nm.

In another aspect, the invention provides a pharmaceutical composition, comprising a nanoparticle of the invention.

In certain embodiments, the nanoparticle is in the form of a dry powder.

In certain embodiments, the composition further includes a pharmaceutically acceptable carrier.

In certain embodiments of the composition the nanoparticle is stably suspended in an aqueous medium. In certain of these embodiments, the composition further comprises a particle size stabilizing agent.

In certain embodiments, the composition is a pharmaceutical composition for injection and comprises a nanoparticle of the invention a pharmaceutically acceptable carrier.

In a further aspect, the invention provides a unit dosage form for treating in an individual that includes a nanoparticle of the invention and a pharmaceutically acceptable carrier.

In another aspect of the invention, a kit is provided. In one embodiment, the kit comprises a container that includes a nanoparticle of the invention, and a container comprising a pharmaceutically acceptable carrier for reconstituting the nanoparticle. In another embodiment, the kit comprises a container that includes a nanoparticle of the invention suspended in a pharmaceutically acceptable carrier. The kits optionally include instructions for using the kit in treating a disease or condition.

In a further aspect of the invention, methods of treating a disease or condition in an individual are provided. In certain embodiments, the methods comprise administering to an individual in need thereof an effective amount of the nanoparticle of the invention. In certain embodiments, the disease or condition is a proliferative disease or condition. In certain embodiments, the therapeutic agent is paclitaxel and the disease is a disease treatable by administering paclitaxel. In certain embodiments, the therapeutic agent is paclitaxel and the disease is a cancer treatable by administering paclitaxel.

In another aspect, methods for preparing a phospholipid-coated therapeutic agent nanoparticle are provided. In one embodiment, the nanoparticle is prepared by a microfluidization-solvent removal method. In another embodiment, the nanoparticle is prepared by a thin film-hydration method.

In certain embodiments, the method for preparing a phospholipid-coated therapeutic agent nanoparticle, comprises subjecting an organic phase containing a therapeutic agent dispersed therein and aqueous medium containing phospholipid to high shear conditions in a high pressure homogenizer to provide a homogenized phospholipid-coated therapeutic agent nanoparticle mixture. In certain embodiments, the method further comprises sterile filtering the mixture. In one embodiment, subjecting the organic phase to high shear conditions comprises using a high pressure homogenizer at a pressure in the range of about 3,000 up to 30,000 psi. In certain embodiments, the method further comprises removing the organic phase from the mixture. In certain embodiments, the method further comprises removing the aqueous medium from the mixture. In certain embodiments, removing the aqueous medium from the mixture comprises lyophilizing the mixture to provide a nanoparticle powder.

In other embodiments, the method for preparing a phospholipid-coated therapeutic agent nanoparticle, comprises dissolving a therapeutic agent and a phospholipid in an organic phase to provide a solution, concentrating the solution to dryness to provide a film, and hydrating the film with water to provide a aqueous suspension of phospholipid-coated therapeutic agent nanoparticles. In certain embodiments, the organic phase is ethanol. In certain embodiments, concentrating the solution to dryness comprises rotary evaporation. In certain embodiments, the water is deionized water. In certain embodiments, the method further comprises sterile filtering the aqueous suspension.

In certain embodiments, the methods of the invention provide nanoparticles of the invention.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 7 compares particle size (at t=0) and paclitaxel incorporation (%) for representative phospholipid-coated therapeutic agent (paclitaxel) nanoparticles of the invention prepared by microfluidization and thin film evaporation methods.

DETAILED DESCRIPTION OF THE INVENTION

Figure 1:
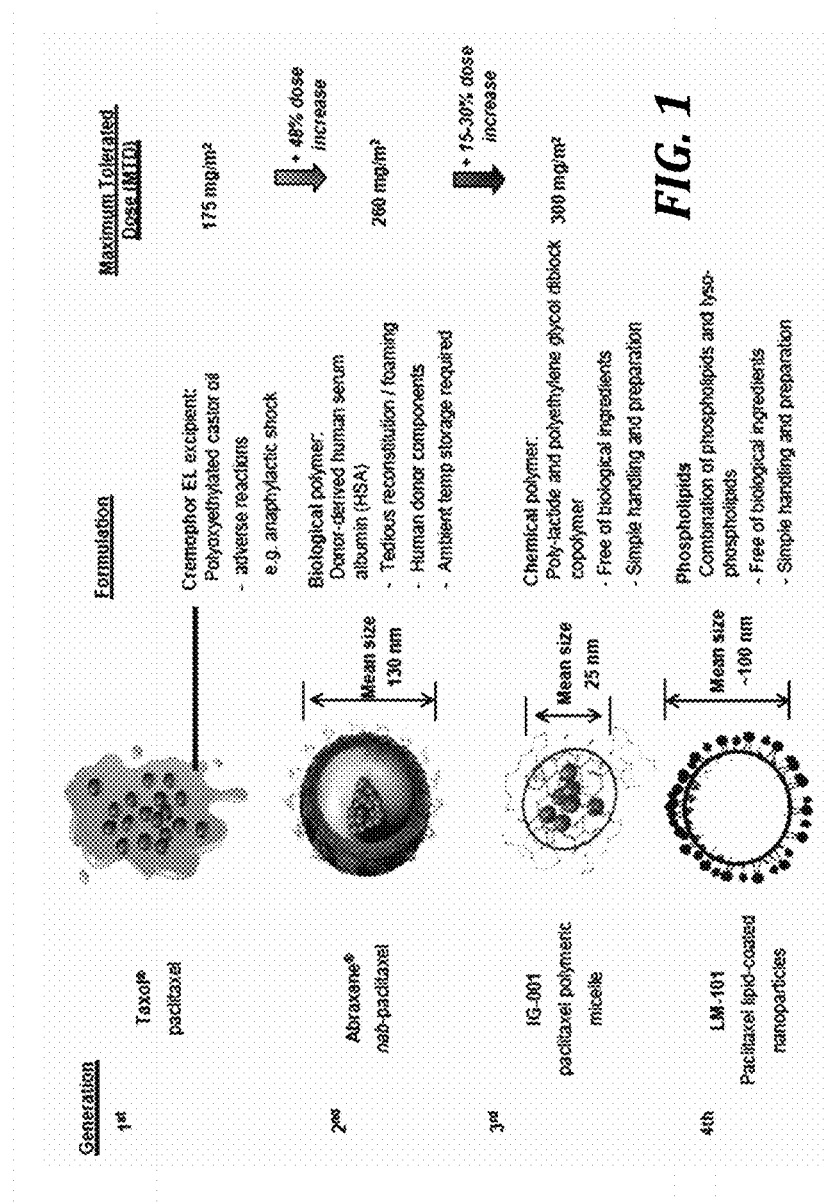
FIG. 1 is a schematic illustration comparing the evolution of formulations of paclitaxel therapy.

The present invention provides phospholipid-coated therapeutic agent nanoparticles suitable for administration by injection, pharmaceutical compositions that include the nanoparticle, methods for treating diseases and conditions treatable by the therapeutic agents, and methods for making the nanoparticles.

Phospholipid-Coated Therapeutic Agent Nanoparticle

In one aspect, the invention provides phospholipid-coated therapeutic agent nanoparticle.

In one embodiment, the phospholipid-coated therapeutic agent nanoparticle, comprises a particulate therapeutic agent coated with one or more phospholipids, wherein the nanoparticle is stable in aqueous delivery vehicles for administration (e.g., vehicles for injection) and releases the therapeutic agent substantially instantaneously upon exposure to or contact with a physiological fluid. As used herein, the term "substantially instantaneously" refers to release of the therapeutic agent from the nanoparticle within about 1 second, within about 2 seconds, within about 5 seconds, within about 10 seconds, or within about 30 seconds after contact with a physiological fluid, such as blood, serum, plasma (e.g., intravenous injection).

In another embodiment, the phospholipid-coated therapeutic agent nanoparticle comprises a particulate therapeutic agent coated with one or more phospholipids, wherein the nanoparticle is as stable in aqueous delivery vehicles for administration as synthetic polymeric micelles containing a therapeutic agent (Genexol-PM®, Cynviloq®) and is as effective in releasing the therapeutic agent under physiological conditions as a human-serum albumin-coated therapeutic agent (Abraxane®).

In a further embodiment, the phospholipid-coated therapeutic agent nanoparticle comprises a particulate therapeutic agent coated with one or more phospholipids, wherein the phospholipid is a mono-acylphospholipid. In this embodiment, with regard to phospholipid, the nanoparticle may include only a mono-acylphospholipid, or may further include a diacylphospholipid.

In another embodiment, the phospholipid-coated therapeutic agent nanoparticle comprises a particulate therapeutic agent coated with one or more phospholipids, wherein the phospholipid comprises a mono-acylphospholipid and a diacylphospholipid.

In a further embodiment, the phospholipid-coated therapeutic agent nanoparticle comprises a particulate therapeutic agent coated with one or more phospholipids, wherein the phospholipid is a diacylphospholipid having a fatty acid component having from 10 to 16 carbon atoms. In this embodiment, with regard to phospholipid, the nanoparticle may further include a mono-acylphospholipid.

In another embodiment, the phospholipid-coated therapeutic agent nanoparticle comprises a particulate therapeutic agent coated with one or more phospholipids, wherein the nanoparticle is substantially electronically neutral based on phospholipid composition.

In a further embodiment, the phospholipid-coated therapeutic agent nanoparticle consists essentially of a particulate therapeutic agent coated with one or more phospholipids.

In another embodiment, the phospholipid-coated therapeutic agent nanoparticle consisting of a particulate therapeutic agent coated with one or more phospholipids.

As noted above, the invention provides a phospholipid-coated therapeutic agent nanoparticle. As used herein, "phospholipid-coated therapeutic agent nanoparticle" refers to a nanoparticle comprising a therapeutic agent in particulate form coated with one or more phospholipids. In the nanoparticle of the invention, the phospholipid coating the particulate therapeutic agent advantageously stabilizes the therapeutic agent and facilitates its effective administration.

The phospholipid-coated therapeutic agent nanoparticle advantageously provides for the effective formulation and delivery of hydrophobic or substantially water insoluble therapeutic agents. Therapeutic agents advantageously formulated as nanoparticles of the invention include hydrophobic or substantially water-insoluble pharmacologically active agents (i.e., any bioactive agent having limited solubility in an aqueous or hydrophilic environment). For example, the solubility in water of these agents at 20-25° C. may be less than about 5, 2, 1, 0.5, 0.2, 0.1, 0.05, 0.02, or 0.01 mg/mL.

The character of therapeutic agents appropriate as candidate therapeutic agents that benefit from formulation as a nanoparticle of the invention include therapeutic agents, such as chemotherapeutic agents, defined by their octanol/water partition coefficient X log P (Wang et al. Chem. Inf. Comput. Sci. 1997, 37, 615-621). For example, the coefficient for paclitaxel is 3.0. In the practice of the invention, therapeutic agents with X log P greater than 2.0 are excellent candidates for incorporation into the nanoparticles of the invention. This characteristic includes over half of the approved pharmaceutical agents currently employed for parenteral administration. As used herein, the terms "hydrophobic" and "substantially water-insoluble" and "poorly water-soluble" refer to therapeutic agents having an octanol/water partition coefficient X log P greater than 2.0, and in certain embodiments greater than 3.0, and in other embodiments greater than 4.0.

Representative therapeutic agents include analgesics/antipyretics, anesthetics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antianginal agents, antipsychotic agents, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines/antipruritics, agents useful for calcium regulation, antibacterial agents, antiviral agents, antimicrobials, anti-infectives, bronchodialators, hormones, hypoglycemic agents, hypolipidemic agents, proteins, nucleic acids, agents useful for erythropoiesis stimulation, antiulcer/antireflux agents, antinauseants/antiemetics, and oil-soluble vitamins.

In certain embodiments, the therapeutic agent is an antineoplastic selected from adriamycin, cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, teniposide, daunomycin, indomethacin, biphenyl dimethyl dicarboxylate, interferon, camptothecin and derivatives thereof, phenesterine, paclitaxel and derivatives thereof, docetaxel and derivatives thereof, epothilones and derivatives thereof, vinblastine, vincristine, tamoxifen, etoposide, or piposulfan. Representative antineoplastic agents include taxanes and their derivatives, such as paclitaxel.

In certain embodiments, the therapeutic agent is an immunosuppressive agent selected from cyclosporine, azathioprine, mizoribine, or FK506 (tacrolimus).

The therapeutic agent nanoparticle of the invention includes one or more phospholipids coating the therapeutic agent. As used herein, the term "phospholipid" refers to a class of lipids having a hydrophobic tail (e.g., one or two) and a phosphate head group. Hydrophilicity is conferred to the phospholipid by it phosphate head group and hydrophobicity is conferred to the phospholipid by apolar groups that include long-chain saturated and unsaturated aliphatic hydrocarbon groups and such groups substituted by one or more aromatic, cycloaliphatic, or heterocyclic groups (e.g., fatty acid acyl groups).

As used herein, the term "phospholipid" refers to phosphatidic acids, phosphoglycerides, and phosphosphingolipids. Phosphatidic acids include a phosphate group coupled to a glycerol group, which may be mono- or diacylated. Phosphoglycerides (or glycerophospholipids) include a phosphate group intermediate an organic group (e.g., choline, ethanolamine, serine, inositol) and a glycerol group, which may be mono- or diacylated. Phosphosphingolipids (or sphingomyelins) include a phosphate group intermediate an organic group (e.g., choline, ethanolamine) and a sphingosine (non-acylated) or ceramide (acylated) group.

It will be appreciated that in certain embodiments, the phospholipids useful in the compositions and methods of the invention include their salts (e.g., sodium, ammonium). For phospholipids that include carbon-carbon double bonds, individual geometrical isomers (cis, trans) and mixtures of isomers are included.

Representative phospholipids include phosphatidylcholines, phosphatidylethanolamines, phosphatidylglycerols, phosphatidylserines, phosphatidylinositols, and phosphatidic acids, and their lysophosphatidyl (e.g., lysophosphatidylcholines and lysophosphatidylethanolamine) and diacyl phospholipid (e.g., diacylphosphatidylcholines, diacylphosphatidylethanolamines, diacylphosphatidylglycerols, diacylphosphatidylserines, diacylphosphatidylinositols, and diacylphosphatidic acids) counterparts.

The acyl groups of the phospholipids may be the same or different. In certain embodiments, the acyl groups are derived from fatty acids having $C_{10}$-$C_{24}$ carbon chains (e.g., acyl groups such as decanoyl (C10), dodecanoyl (also known as lauroyl) (C12), tetradecanoyl (also known as myristoyl) (C14), hexadecanoyl (also known as palmitoyl) (C16), octadecanoyl (also known as stearoyl) (C18), oleoyl, linoleoyl, linolenoyl, arachidonoyl groups).

Representative diacylphosphatidylcholines (i.e., 1,2-diacyl-sn-glycero-3-phosphocholines) include distearoylphosphatidylcholine (DSPC), dioleoylphosphatidylcholine (DOPC), dipalmitoylphosphatidylcholine (DPPC), dilinoleoylphosphatidylcholine (DLPC), palmitoyloleoylphosphatidylcholine (POPC), palmitoyllinoleoylphosphatidylcholine, stearoyllinoleoylphosphatidylcholine stearoyloleoylphosphatidylcholine, stearoylarachidoylphosphatidylcholine, didecanoylphosphatidylcholine (DDPC), didodecanoylphosphatidylcholine, dierucoylphosphatidylcholine (DEPC), dilinoleoylphosphatidylcholine (DLOPC), dimyristoylphosphatidylcholine (DMPC), myristoylpalmitoylphosphatidylcholine (MPPC), myristoylstearoylphosphatidylcholine (MSPC), stearoylmyristoylphosphatidylcholine (SMPC), palmitoylmyristoylphosphatidylcholine (PMPC), palmitoylstearoylphosphatidylcholine (PSPC), stearoylpalmitoylphosphatidylcholine (SPPC), and stearoyloleoylphosphatidylcholine (SOPC).

Representative diacylphosphatidylethanolamines (i.e., 1,2-diacyl-sn-glycero-3-phosphoethanolamines) include dioleoylphosphatidylethanolamine (DOPE), dipalmitoylphosphatidylethanolamine (DPPE), distearoylphosphatidylethanolamine (DSPE), dilauroylphosphatidylethanolamine (DLPE), dimyristoylphosphatidylethanolamine (DMPE), dierucoylphosphatidylethanolamine (DEPE), didecanoylphosphatidylethanolamine, didodecanoylphosphatidylethanolamine, and palmitoyloleoylphosphatidylethanolamine (POPE).

Representative diacylphosphatidylglycerols (i.e., 1,2-diacyl-sn-glycero-3-phosphoglycerols) include dioleoylphosphatidylglycerol (DOPG), dipalmitoylphosphatidylglycerol (DPPG), dierucoylphosphatidylglycerol (DEPG), dilauroylphosphatidylglycerol (DLPG), dimyristoylphosphatidylglycerol (DMPG), distearoylphosphatidylglycerol (DSPG), didecanoylphosphatidylglycerol, didodecanoylphosphatidylglycerol, and palmitoyloleoylphosphatidylglycerol (POPG).

Representative diacylphosphatidylserines (i.e., 1,2-diacyl-sn-glycero-3-phosphoserines) include dilauroylphosphatidylserine (also known as didodecanoylphosphatidylserine) (DLPS), dioleoylpho sphatidylserine (DOPS), dipalmitoylphosphatidylserine (DPPS), didecanoylpho sphatidylserine, and distearoylphosphatidylserine (DSPS).

Representative diacylphosphatidic acids (i.e., 1,2-diacyl-sn-glycero-3-phosphates) include dierucoylphosphatidic acid (DEPA), dilauroylphosphatidic acid (also known as didodecanoylphosphatidic acid) (DLPA), dimyristoylphosphatidic acid (DMPA), dioleoylphosphatidic acid (DOPA), dipalmitoylphosphatidic acid (DPPA), didecanoylphosphatidic acid, and distearoylphosphatidic acid (DSPA).

Representative phospholipids include phosphosphingolipids such as ceramide phosphoryllipid, ceramide phosphorylcholine, and ceramide phosphorylethanolamine. The nanoparticle of the invention includes two or more different phospholipids.

In certain embodiments, the nanoparticle includes two different phospholipids. In other embodiments, the nanoparticle includes three different phospholipids. In further embodiments, the nanoparticle includes four different phospholipids.

In certain embodiments, the nanoparticle of the invention further includes a sterol (e.g., cholesterol).

As noted above, in certain embodiments, the phospholipid is a diacylphospholipid. Representative diacylphospholipids include diacylphosphatidylcholines, diacylphosphatidylethanolamines, diacylphosphatidylglycerols, diacylphosphatidylserines, diacylphosphatidylinositols, and diacylphosphatidic acids.

In certain embodiments, the diacylphospholipid (e.g., phosphatidylcholine) has a fatty acid component (acyl groups) having from 10 to 22 carbons (e.g., 10, 12, 14, 16, 18, 20, 22 carbons). In certain embodiments, the diacylphospholipid has a fatty acid component having from 10 to 20 carbons (e.g., 10, 12, 14, 16, 18, 20 carbons). In other embodiments, the diacylphospholipid has a fatty acid component having from 10 to 16 carbons (e.g., 10, 12, 14, 16 carbons). In further embodiments, the diacylphospholipid has a fatty acid component having from 10 to 14 carbons (e.g., 10, 12, 14 carbons). In yet other embodiments, the diacylphospholipid has a fatty acid component having from 10 to 12 carbons (e.g., 10, 12 carbons). In certain embodiments, the diacylphospholipid has a fatty acid component having 10 carbons. It will be appreciated that in certain of the embodiments noted above, each of the fatty acid components in the diacylphospholipid has the same number of carbons (e.g., 10, 12, 14, 16, 18, 20, 22 carbons), such as 1,2-didecanoylphosphatidylcholine, and that in other of the embodiments noted above, each of the fatty acid components in the diacylphospholipid has a different number of carbons, such as stearoyloleoylphosphatidylcholine.

In certain embodiments, the phospholipid is a phosphatidylcholine. Suitable phosphatidylcholines include phosphatidylcholines having a fatty acid component (acyl groups) having from 10 to 22 carbons (e.g., 10, 12, 14, 16, 18, 20, 22 carbons). In certain embodiments, the phosphatidylcholine has a fatty acid component having from 10 to 20 carbons (e.g., 10, 14, 16, 18, 20 carbons). In other embodiments, the phosphatidylcholine has a fatty acid component having from 10 to 16 carbons (e.g., 10, 12, 14, 16 carbons). In further embodiments, the phosphatidylcholine has a fatty acid component having from 10 to 14 carbons (e.g., 10, 12, 14 carbons). In yet other embodiments, the phosphatidylcholine has a fatty acid component having from 10 to 12 carbons (e.g., 10, 12 carbons). In certain embodiments, the phosphatidylcholine has a fatty acid component having 10 carbons. Representative phosphatidylcholines include those illustrated in FIG. 2 (e.g., PC-12, PC-14, PC-16, PC-18, PC-20) and PC-10 (not shown). It will be appreciated that the fatty acid component of a particular phospholipid need not be the same (i.e., diacyl with different acyl groups).

In certain embodiments, the phospholipid is an electronically neutral phospholipid having, for example, a negatively charged phosphate group and a positively charged amine group (e.g., a phosphatidylcholine or phosphatidylethanolamine). In other embodiments, the phospholipid is an electronically negative phospholipid having a negatively charged phosphate group (e.g., a phosphatidylglycerol).

As noted above, in certain embodiments, the phospholipid is a lysophospholipid. In certain of these embodiments, the lysophospholipid is a mono-acylphospholipid. Representative lysophospholipids include lysophosphatidylcholines, lysophosphatidylethanolamines, lysophosphatidylglycerols, lysophosphatidylserines, lysophosphatidylinositols, and lysophosphatidic acids (e.g., mono-acylphosphatidyl compounds).

In certain embodiments, the mono-acylphospholipid (e.g., lysophosphatidylcholine) has a fatty acid component (acyl group) having from 10 to 22 carbons (e.g., 10, 12, 14, 16, 18, 20, 22 carbons). In certain embodiments, the mono-acylphospholipid has a fatty acid component having from 10 to 20 carbons (e.g., 10, 12, 14, 16, 18, 20 carbons). In other embodiments, the mono-acylphospholipid has a fatty acid component having from 10 to 16 carbons (e.g., 10, 12, 14, 16 carbons). In further embodiments, the mono-acylphospholipid has a fatty acid component having from 10 to 14 carbons (e.g., 10, 12, 14 carbons). In yet other embodiments, the mono-acylphospholipid has a fatty acid component having from 10 to 12 carbons (e.g., 10, 12 carbons). In certain embodiments, the mono-acylphospholipid has a fatty acid component having 10 carbons.

In certain embodiments, the phospholipid is a lysophosphatidylcholine. Suitable lysophosphatidylcholines include lysophosphatidylcholines having a fatty acid component (acyl group) having from 10 to 22 carbons (e.g., 10, 12, 14, 16, 18, 20, 22 carbons). In certain embodiments, the phosphatidylcholine has a fatty acid component having from 10 to 20 carbons (e.g., 10, 14, 16, 18, 20 carbons). In other embodiments, the lysophosphatidylcholine has a fatty acid component having from 10 to 16 carbons (e.g., 10, 12, 14, 16 carbons). In further embodiments, the lysophosphatidylcholine has a fatty acid component having from 10 to 14 carbons (e.g., 10, 12, 14 carbons). In yet other embodiments, the lysophosphatidylcholine has a fatty acid component having from 10 to 12 carbons (e.g., 10, 12 carbons). In certain embodiments, the lysophosphatidylcholine has a fatty acid component having 10 carbons. Representative lysophosphatidylcholines include those illustrated in FIG. 2 (e.g., lyso-PC-12, lyso-PC-14, lyso-PC-16, lyso-PC-20) and lyso-PC-10.

In certain embodiments, the lysophospholipid is an electronically neutral lysophospholipid having, for example, a negatively charged phosphate group and a positively charged amine group (e.g., a lysophosphatidylcholine or lysophosphatidylethanolamine). In other embodiments, the lysophospholipid is an electronically negative lysophospholipid having a negatively charged phosphate group (e.g., a lysophosphatidylglycerol).

In certain embodiments, the nanoparticle of the invention includes a diacylphospholipid and a mono-acylphospholipid. In certain of these embodiments, the nanoparticle of the invention includes a phosphatidylcholine and a lysophosphatidylcholine.

The ratio of di- to mono-acylphospholipid (e.g., phosphatidylcholine to lysophosphatidylcholine) is from about 1:99 w/w percent to about 99:1 w/w percent. In certain embodiments, the ratio of di- to mono-acylphospholipid (e.g., phosphatidylcholine to lysophosphatidylcholine) is about 10:90 to about 90:10 w/w percent. In other embodiments, the ratio of di- to mono-acylphospholipid (e.g., phosphatidylcholine to lysophosphatidylcholine) is about 20:80 to about 80:20 w/w percent. In further embodiments, the ratio of di- to mono-acylphospholipid (e.g., phosphatidylcholine to lysophosphatidylcholine) is about 30:70 to about 70:30 w/w percent. In other embodiments, the ratio of di- to mono-acylphospholipid (e.g., phosphatidylcholine to lysophosphatidylcholine) is about 40:60 to about 60:40 w/w percent. In certain embodiments, the ratio of di- to mono-acylphospholipid (e.g., phosphatidylcholine to lysophosphatidylcholine) is about 50:50 w/w percent. In certain embodiments, the ratio of di- to mono-acylphospholipid (e.g., phosphatidylcholine to lysophosphatidylcholine) is from about 90:10 to about 60:40 w/w percent. In other embodiments, the ratio of di- to mono-acylphospholipid (e.g., phosphatidylcholine to lysophosphatidylcholine) is from about 90:10 to about 70:30 w/w percent. In further embodiments, the ratio of di- to mono-acylphospholipid (e.g., phosphatidylcholine to lysophosphatidylcholine) is about 80:20 w/w percent.

In certain embodiments of the invention in which the nanoparticle includes a diacylphospholipid (e.g., a phosphatidylcholine) and a mono-acylphospholipid (e.g., lysophosphatidylcholine), the fatty acid components of the di- and mono-acylphospholipids are the same. For example, each of the di- and mono-acylphospholipids includes C10 (decanoyl) fatty acid components, each includes C12 (dodecanoyl) fatty acid components, each includes C14 (tetradecanoyl) fatty acid components, each includes C16 (hexadecanoyl) fatty acid components, or each includes C18 (dodecanoyl) fatty acid components. Alternatively, in other embodiments, the fatty acid components of the di- and mono-acylphospholipids are different (e.g., the diacylphospholipid includes C10 fatty acid components and the mono-acylphospholipid includes a C12 fatty acid component.

The phospholipid and therapeutic agent in the composition can be associated in various manners. For example, in some embodiments, the phospholipid is in admixture with the therapeutic agent. In some embodiments, the phospholipid encapsulates or entraps the therapeutic agent. In some embodiments, the phospholipid is bound (e.g., non-covalently bound) to the therapeutic agent.

Particle Size.

The nanoparticles of the invention have an average or mean diameter of no greater than about any of about 1000, 900, 800, 700, 600, 500, 400, 300, 200, or 100 nm. In some embodiments, the average or mean diameter of the particles is between about 30-300 nm. In some embodiments, the average or mean diameter of the particles is between about 20-200 nm. In some embodiments, the average or mean diameter of the particles is between about 80-200 nm. In certain embodiments, the average or mean diameter of the particles is between about 30-180 nm. In some embodiments, the average or mean diameter of the particles is between about 40-160 nm. In certain embodiments, the average or mean diameter of the particles is between about 80-140 nm. In other embodiments, the average or mean diameter of the particles is between about 90-120 nm. In some embodiments, the particles are sterile-filterable.

Particle Charge.

Depending on the composition of the phospholipids of the nanoparticle, the nanoparticle can be electronically neutral or charged. In certain embodiments, when the nanoparticle includes only phospholipids (e.g., di- and/or mono-acylphospholipids) that are electronically neutral (e.g., a phosphatidylcholine, lysophosphatidylcholine, phosphatidylethanolamine, and/or lyso phosphatidylethanolamine, each having a negatively charged phosphate group and a positively charged amine group), the nanoparticle is electronically neutral, at least in regard to the nanoparticle's phospholipid component. In other embodiments, when the nanoparticle includes a phospholipid (e.g., di- and/or mono-acylphospholipid) that is negatively charged (e.g., a phosphatidylglycerol having a negatively charged phosphate group and no corresponding positively charged group), the nanoparticle is electronically negative, at least in regard to the nanoparticle's phospholipid component.

In certain embodiments, the nanoparticle is electronically neutral in regard to the nanoparticle's phospholipid content. In other embodiments, the nanoparticle is electronically negative (negatively charged) in regard to the nanoparticle's phospholipid content.

Representative nanoparticles of the invention demonstrate pharmacokinetic bioequivalence to Abraxane® with large volume of distribution, low AUC, and low Cmax in comparison to solvent-based paclitaxel formulations, such as Taxol® or Tocosol®. Cynviloq® provides the desired pharmacokinetic bioequivalence to Abraxane®, but suffers from undesirable hypersensitivity to its excipient/polymer. This prompted the replacement of mPEG-PDLLA in Cynviloq® with naturally-occurring phospholipids.

Phospholipid-Coated Nanoparticle Characteristics

In one aspect, the invention provides a phospholipid-coated therapeutic agent nanoparticle that includes a particulate therapeutic agent coated with one or more phospholipids. The phospholipid nanoparticle of the invention and formulations that include the nanoparticles are advantageous for several reasons.

Figure 3:
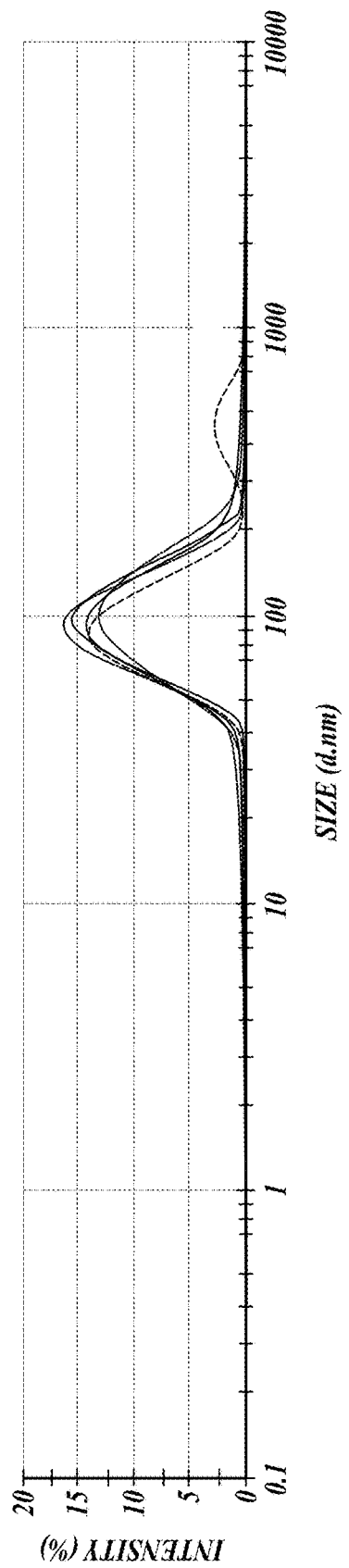
FIG. 3 is a graph comparing nanoparticle size and size distribution of representative phospholipid-coated therapeutic agent nanoparticles of the invention prepared by a microfluidization-solvent evaporation method.
Figure 4:
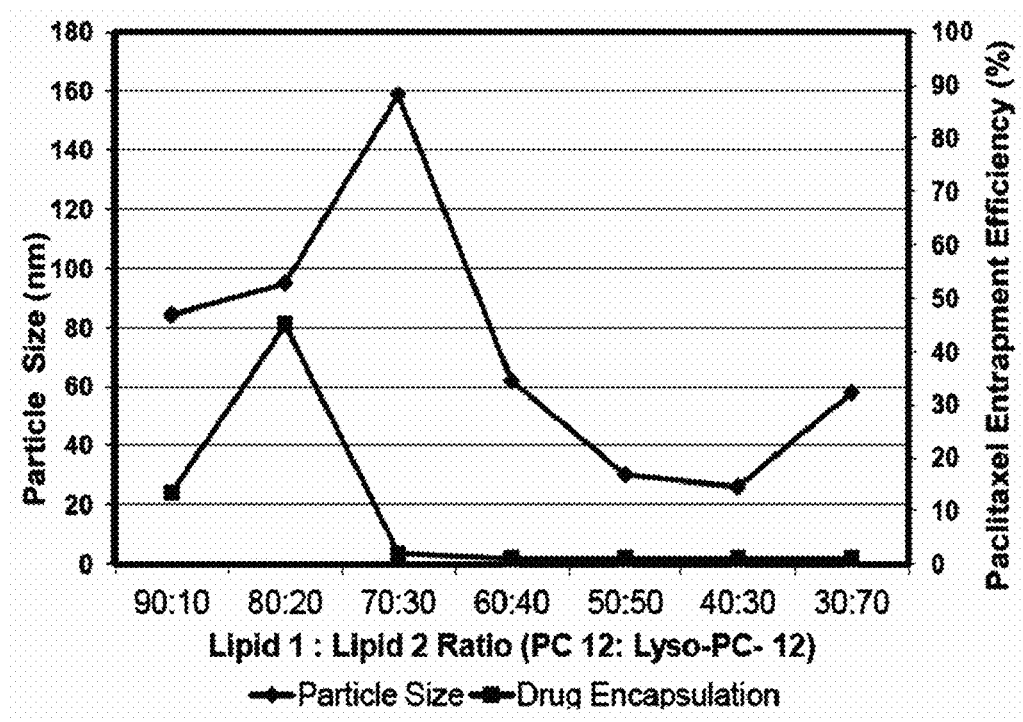
FIG. 4 compares the effect of phospholipid and lyso-phospholipid ratio on nanoparticle size and therapeutic agent entrapment efficiency for representative phospholipid-coated therapeutic agent (paclitaxel) nanoparticles of the invention.

The nanoparticle of the invention provides the desirable benefits of stable particle size and therapeutic agent loading. Representative particles of the invention have an average diameter ($Z_{av}$) between from about 20-200 nm to about 90-120 nm. FIG. 3 illustrates the size and size distribution of a representative paclitaxel particle coated with a combination of di- and mono-acylphospholipids. These particles have an average diameter of about 100 nm with a polydispersity index of about 0.1. As shown in FIG. 4, therapeutic agent entrapment efficiency (drug loading) and particle size are correlated and optimized for particles with di- to mono-acylphospholipid ratio from about 90:10 to about 70:30. Particle size, therapeutic agent (paclitaxel) content (entrapment efficiency %), and phospholipid composition for representative nanoparticles of the invention are summarized in Table 2, Table 3, and Table 4 (FIG. 7). In certain embodiments, optimized therapeutic agent entrapment efficiency is observed for nanoparticles of the invention having an average diameter from about 90-120 nm (e.g., about 100 nm), a polydispersity index of about 0.1, and having a phospholipid composition that is a combination of di- and mono-acylphospholipids in the ratio of from about 90:10 to about 70:30

(e.g., about 80:20 didodecanoylphosphatidylcholine:didodecanoyllysophosphatidylcholine).

Figure 9:
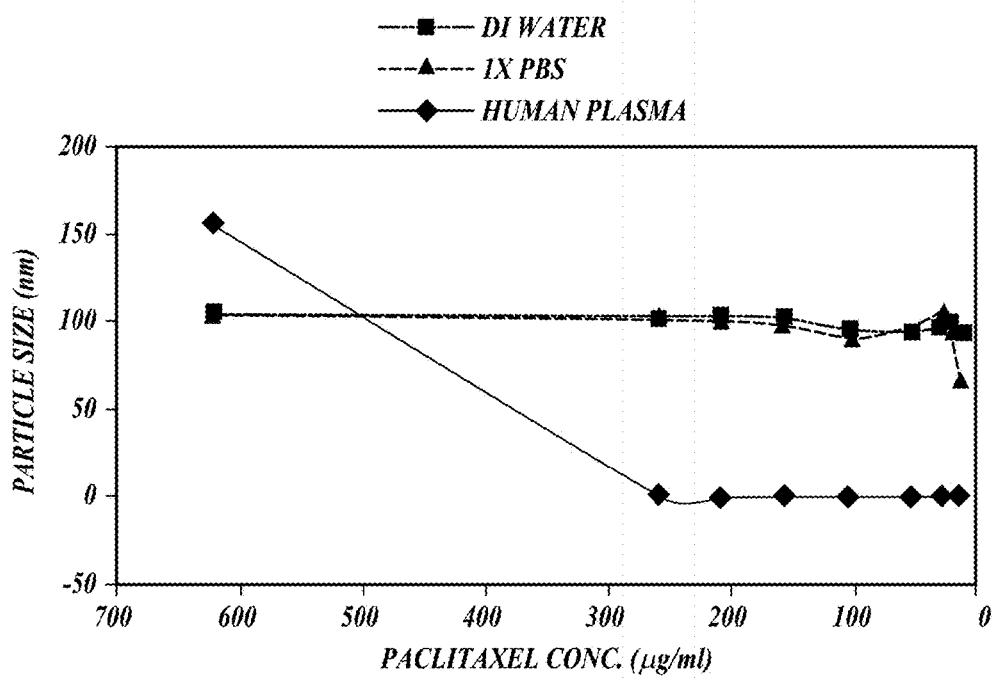
FIG. 9 compares dissolution of representative phospholipid-coated therapeutic agent (paclitaxel) nanoparticles of the invention in deionized water (DI), phosphate buffered saline (PBS), and human plasma (50 mg/mL human serum albumin/PBS) showing particle size (nm) as a function of paclitaxel concentration (μg/mL).
Figure 13:
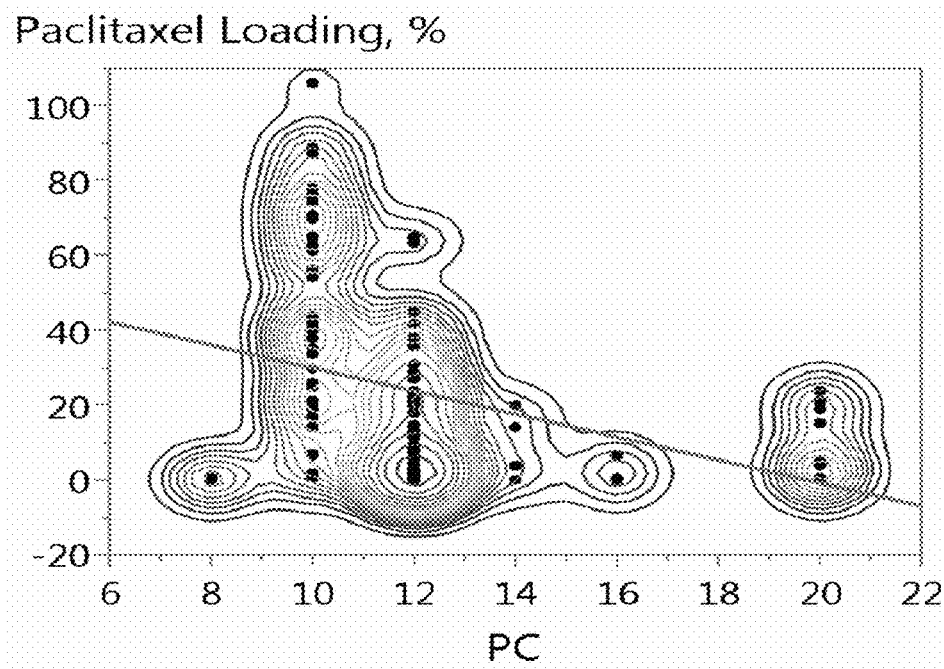
FIG. 13 compares paclitaxel loading (%) for representative phospholipid-coated therapeutic agent (paclitaxel) nanoparticles of the invention as a function of PC carbon length (6-22) prepared by the thin film-hydration method (Method 2).

In the practice of the invention, the selection of phospholipids effective to provide optimized nanoparticles was made based on therapeutic agent loading, particle size and size stability, and the therapeutic agent release profile [effective release/particle dissolution under physiological conditions (plasma) and stability under administration conditions (PBS or DI)]. The selection of phospholipids was not made based on solubility of the therapeutic agent in the phospholipid. Therapeutic agent (paclitaxel) loading as a function of phospholipid fatty acid component carbon number (C8-C20) is shown in FIG. 13. Optimum loading was observed for phospholipids having a fatty acid component carbon number (C10-C14) (e.g., di- and monoacylphospholipids having fatty acid components having from 10 to 14 carbons, such as phosphatidylcholines and lysophosphatidylcholines). Advantageous size and size stability for representative nanoparticles was demonstrated as shown in FIGS. 9 and 10C (see DI and PBS traces).

Representative nanoparticles of the invention demonstrate therapeutic agent release (particle dissolution) profiles that combine the desirable properties of clinically effective formulations: Abraxane® and Genexol-PM® (Cynviloq®). In contrast to the phospholipid-coated nanoparticles of the invention, Abraxane® is a nanoparticle coated with human serum albumin and Genexol-PM® is a nanoparticle in the form of a synthetic polymeric micelle. Abraxane® provides desirable plasma instability (drug release), but suffers from undesirable instability in delivery vehicles (e.g., PBS) (see FIG. 10A). Genexol-PM® provides desirable stability in delivery vehicles and desirable instability in plasma (see FIG. 10B). Representative phospholipid-coated nanoparticles of the invention advantageously demonstrate stability in delivery vehicles (aqueous vehicles for intravenous, intravesicle, and intraperitoneal administration, such as aqueous buffers (saline), dextrose solutions, and deionized water useful in solutions for injection) and desirable plasma instability for therapeutic agent release in plasma (see FIG. 10C).

In certain of the embodiments noted above, the nanoparticles of the invention are not negatively charged.

In certain of the embodiments noted above, neither the nanoparticles nor the nanoparticle compositions of the invention include PEG-based cryoprotectants (e.g., PEG-6000).

Figure 16:
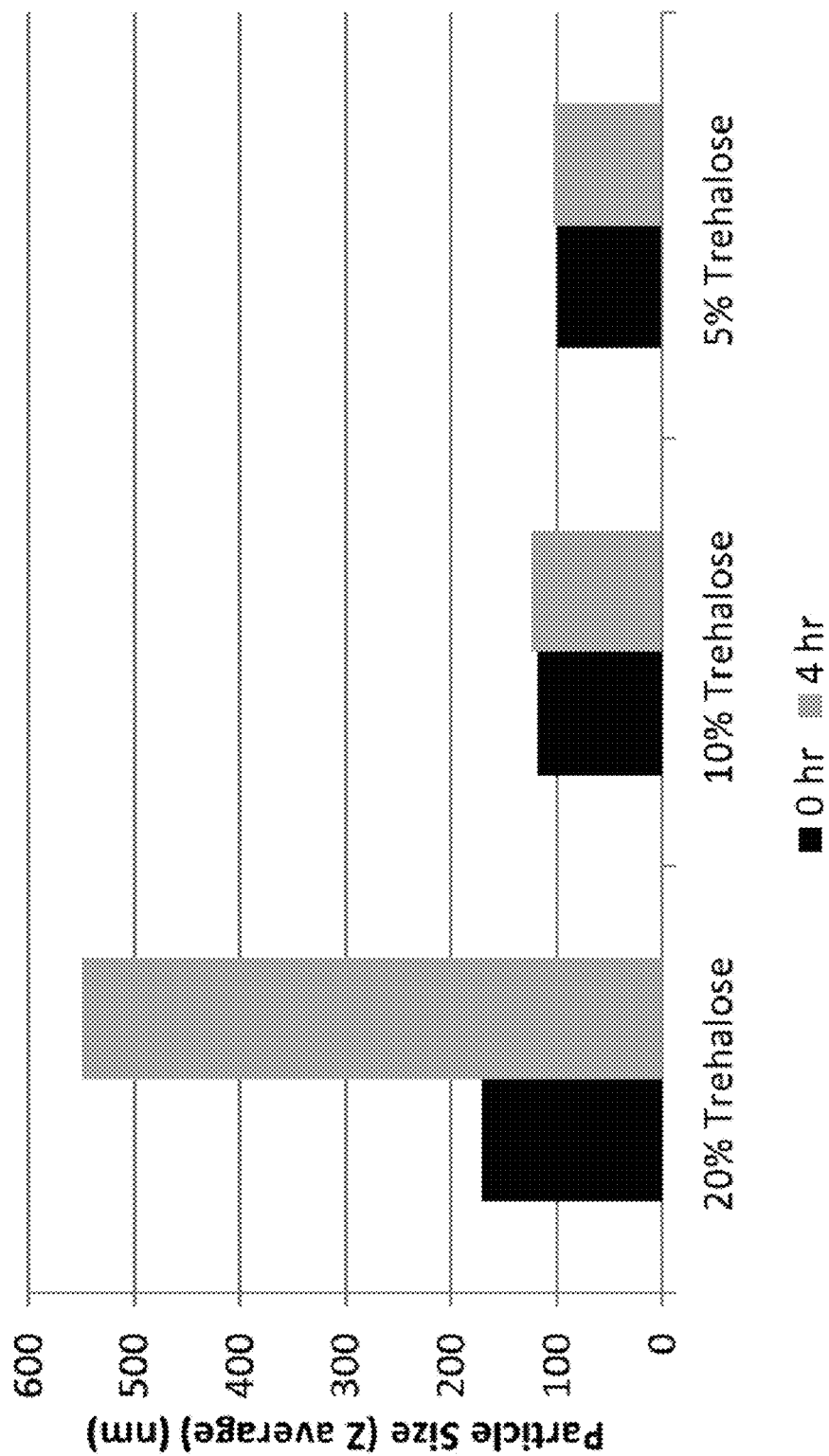
FIG. 16 compares particle size as a function of time (t=0 and 4 hr) after reconstitution with 3.2 mM histidine buffer at pH 5.5 for representative phospholipid-coated therapeutic agent (paclitaxel) nanoparticles of the invention, PC-coated paclitaxel nanoparticle manufactured by thin film-hydration method (LM-101).

The representative nanoparticles noted above are readily formulated in delivery vehicles effective for therapeutic administration. These formulations advantageously demonstrate particle size stability. Particle size stability can be an important factor for therapeutic administration of nanoparticles. In embodiments where the nanoparticles of the invention are provided as a lyophilized powder, the nanoparticles are subsequently reconstituted in an aqueous delivery vehicle prior (e.g., immediately prior) to administration to the subject. Reconstitution of nanoparticles in the aqueous vehicle, optionally followed by filtration (0.2 μm), provides a formulation that can be subject to particle size instability (e.g., particle aggregation, particle dissolution, therapeutic agent release). As shown in FIG. 16, particle size of representative nanoparticles of the invention can be stabilized by suitable additives (e.g., particle size stabilizers, such as trehalose, for example, about 5% w/w trehalose). Accordingly, in certain embodiments, these formulations of the invention include a particle size stabilizer. Representative particle size stabilizers include buffering agents to control pH, surfactants to inhibit protein adsorption to interfaces, preservatives to prevent microbial growth, carbohydrates as bulking agents for lyophilization, polymers to increase solution viscosity, and salts or sugars to stabilize proteins and to obtain physiological tonicity and osmolality. These can be used in the formulations at concentrations from about 1-15% w/w based on the total weight of the formulation.

It will be appreciated that in certain embodiments, the nanoparticles of the invention comprise the components described herein. In certain other embodiments, it will be appreciated that the nanoparticles of the invention consist essentially of the components described herein, and that in these embodiments the nanoparticles do not include any additional component that would material affect the properties of the nanoparticle (e.g., therapeutic function, effect, or other pharmacokinetic properties). In certain further embodiments, it will be appreciated that the nanoparticles of the invention consist of the components described herein, and that in these embodiments the nanoparticles do not include any additional components.

Phospholipid-Coated Therapeutic Agent Nanoparticle Compositions

In another aspect of the invention, phospholipid-coated therapeutic agent nanoparticle compositions are provided. Representative compositions include dry and liquid compositions.

In certain embodiments, the composition comprises a dry (e.g., lyophilized) composition. In other embodiments, the composition is a liquid (e.g., aqueous) composition obtained by reconstituting or resuspending a dry composition. In further embodiments, the composition is an intermediate liquid (e.g., aqueous) composition that can be dried (e.g., lyophilized).

Dry compositions of the invention can be reconstituted, resuspended, or rehydrated to form generally a stable aqueous suspension of particles comprising the therapeutic agent and phospholipid (e.g., phospholipid-coated therapeutic agent). A hydrophobic therapeutic agent is "stabilized" by a phospholipid in an aqueous suspension if it remains suspended in an aqueous medium (e.g., without visible precipitation or sedimentation) for an extended period of time, such as for at least about any of 0.1, 0.2, 0.25, 0.5, 1, 2, 3, 4, 5, 6, 7, 8, 9, 10, 11, 12, 24, 36, 48, 60, or 72 hours. The suspension is generally, but not necessarily, suitable for administration to a subject (e.g., human). The stability of the suspension is in some embodiments evaluated at room temperature (e.g., 20-25° C.) or refrigerated conditions (e.g., 4° C.). Stability can also be evaluated under accelerated testing conditions, such as at a temperature that is higher than about 40° C.

In other embodiments, the composition is a liquid (e.g., aqueous) composition obtained by reconstituting or resuspending a dry composition in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

The amount of phospholipid in the composition described herein will vary depending on the therapeutic agent and other components in the composition. In some embodiments, the composition comprises a phospholipid in an amount that is sufficient to stabilize the therapeutic carrier in an aqueous suspension, for example, in the form of a stable colloidal suspension (e.g., a stable suspension of nanoparticles). In some embodiments, the phospholipid is in an amount that reduces the sedimentation rate of the therapeutic agent in an aqueous medium. For particle-containing compositions, the amount of the phospholipid also depends on the size and density of particles of the therapeutic agent.

In some embodiments, the phospholipid is present in an amount that is sufficient to stabilize the therapeutic agent in an aqueous suspension at a certain concentration. For example, the concentration of the therapeutic agent in the composition is about 0.1 to about 100 mg/ml, including, for example, any of about 0.1 to about 50 mg/ml, about 0.1 to about 20 mg/ml, about 1 to about 10 mg/ml, about 2 to about 8 mg/ml, and about 4 to about 6 mg/ml. In some embodiments, the concentration of the therapeutic agent is at least about any of about 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml. In some embodiments, the phospholipid is present in an amount that avoids use of surfactants (such as Tween 80 or Cremophor or other biocompatible polymers). Thus, in certain embodiments, the compositions of the invention are advantageously free or substantially free of surfactants (such as Tween 80 and Cremophor) and other biocompatible polymers (e.g., serum albumins, such as human serum albumin, and synthetic polymers such as poly(alkylene oxide)-containing polymers as described in U.S. Pat. No. 6,322,805).

In some embodiments, the composition, in liquid form, comprises from about 0.1% to about 50% (w/v) (e.g., about 0.5% (w/v), about 5% (w/v), about 10% (w/v), about 15% (w/v), about 20% (w/v), about 30% (w/v), about 40% (w/v), about 50% (w/v)) of the phospholipid. In some embodiments, the composition, in liquid form, comprises about 0.5% to about 5% (w/v) of the phospholipid.

In some embodiments, the weight ratio of phospholipid to the therapeutic agent is such that a sufficient amount of the therapeutic agent binds to, or is transported by, the cell. While the weight ratio of phospholipid to therapeutic agent can be optimized for different phospholipid and therapeutic agent combinations, generally the weight ratio of phospholipid to therapeutic agent (w/w) is about 0.01:1 to about 100:1, including for example any of about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, and about 9:1. In some embodiments, the phospholipid to therapeutic agent weight ratio is about any of 18:1 or less, such as about any of 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less.

In some embodiments, the phospholipid allows the composition to be administered to a subject (e.g., human) without significant side effects. In some embodiments, the phospholipid is in an amount that is effective to reduce one or more side effects of administration of the therapeutic agent to a human. The term "reducing one or more side effects of administration of the therapeutic agent" refers to reduction, alleviation, elimination, or avoidance of one or more undesirable effects caused by the therapeutic agent, as well as side effects caused by delivery vehicles (such as solvents that render the therapeutic suitable for injection) used to deliver the therapeutic agent. Such side effects include, for example, myelosuppression, neurotoxicity, hypersensitivity, inflammation, venous irritation, phlebitis, pain, skin irritation, peripheral neuropathy, neutropenic fever, anaphylactic reaction, venous thrombosis, extravasation, and combinations thereof. These side effects, however, are merely exemplary and other side effects, or combination of side effects, associated with various therapeutic agents can be reduced.

Other Components in the Compositions.

The compositions described herein can include other agents, excipients, or stabilizers to improve properties of the composition. Examples of suitable excipients and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. Examples of emulsifying agents include tocopherol esters such as tocopheryl polyethylene glycol succinate and the like, Pluronic, emulsifiers based on polyoxyethylene compounds, Span 80 and related compounds, and other emulsifiers known in the art and approved for use in animals or human dosage forms. The compositions can be formulated so as to provide rapid, sustained or delayed release of the active ingredient after administration to the patient by employing procedures well known in the art.

Compositions for administration by injection include those comprising a therapeutic agent as the active ingredient in association with a surface-active agent (or wetting agent or surfactant), or in the form of an emulsion (e.g., as a water-in-oil or oil-in-water emulsion). Other ingredients can be added, for example, mannitol or other pharmaceutically acceptable vehicles, if necessary.

In some embodiments, the composition is suitable for administration to a human. In some embodiments, the composition is suitable for administration to a mammal, such as, in the veterinary context, including domestic pets and agricultural animals. The following formulations and methods are merely exemplary and are in no way limiting. Formulations suitable for oral administration can consist of (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, (d) suitable emulsions, and (e) powders. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Injectable formulations are preferred.

In some embodiments, the composition is formulated to have a pH in the range of about 4.5 to about 9.0, including for example pH in the ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (such as about 7.5 or about 8). The composition can also be made to be isotonic with blood by the addition of a suitable tonicity modifier, such as glycerol.

It will be appreciated that in certain embodiments, the compositions of the invention comprise the components described herein (e.g., may include other component such as described below). In certain other embodiments, it will be appreciated that the compositions of the invention consist essentially of the components described herein, and that in these embodiments the compositions do not include any additional component that would material affect the properties of the nanoparticle (e.g., therapeutic function, effect, or other pharmacokinetic properties). In certain further embodiments, it will be appreciated that the compositions of the invention consist of the components described herein, and that in these embodiments the compositions do not include any additional components.

Articles of Manufacture Comprising Phospholipid-Coated Therapeutic Agent Nanoparticles In further aspects, the invention provides articles of manufacture comprising the compositions described herein in suitable packaging. Suitable packaging for compositions described herein are known in the art, and include, for example, vials (such as sealed vials), vessels (such as sealed vessels), ampules, bottles, jars, flexible packaging (such as sealed Mylar or plastic bags), and the like. These articles of manufacture may further be sterilized and/or sealed.

Also provided are unit dosage forms comprising the compositions described herein. These unit dosage forms can be stored in a suitable packaging in single or multiple unit dosages and may also be further sterilized and sealed.

The present invention also provides kits comprising compositions (or unit dosages forms and/or articles of manufacture) described herein and may further comprise instruction(s) on methods of using the composition, such as uses further described herein. In some embodiments, the kit of the invention comprises the packaging described above. In other embodiments, the kit of the invention comprises the packaging described above and a second packaging comprising a buffer. It may further include other materials desirable from a commercial and user standpoint, including other buffers, diluents, filters, needles, syringes, and package inserts with instructions for performing any methods described herein.

Kits may also be provided that contain sufficient dosages of the therapeutic agent as disclosed herein to provide effective treatment for an individual for an extended period, such as any of a week, 2 weeks, 3 weeks, 4 weeks, 6 weeks, 8 weeks, 3 months, 4 months, 5 months, 6 months, 7 months, 8 months, 9 months or more. Kits may also include multiple unit doses of the therapeutic agent and pharmaceutical compositions and instructions for use and packaged in quantities sufficient for storage and use in pharmacies, for example, hospital pharmacies and compounding pharmacies.

Methods of Using Phospholipid-Coated Therapeutic Agent Nanoparticles

In another aspect, the invention provides methods for using the phospholipid-coated therapeutic agent nanoparticles.

In certain embodiments, the invention provides a method for treating a disease or condition that is responsive to a therapeutic agent comprising administering a composition comprising an effective amount of the phospholipid-coated therapeutic agent nanoparticle. For example, in some embodiments, there is provided a method of treating cancer in an individual (such as human) comprising administering to the individual a composition comprising an effective amount of a antineoplastic therapeutic agent (such as paclitaxel) and a phospholipid protein.

The term "effective amount" used herein refers to an amount of a compound or composition sufficient to treat a specified disorder, condition or disease such as ameliorate, palliate, lessen, and/or delay one or more of its symptoms. In reference to cancers or other unwanted cell proliferation, an effective amount comprises an amount sufficient to cause a tumor to shrink and/or to decrease the growth rate of the tumor (such as to suppress tumor growth). In some embodiments, an effective amount is an amount sufficient to delay development. In some embodiments, an effective amount is an amount sufficient to prevent occurrence and/or recurrence. An effective amount can be administered in one or more administrations.

The compositions of the invention (e.g., where the therapeutic agent is an anti-proliferative agent, such as paclitaxel) are effective for treating proliferative diseases including cancers, restenosis, and fibrosis, among others. When the therapeutic agent is paclitaxel, the compositions are effective for treating diseases and conditions treatable by administering paclitaxel.

Cancers to be treated by compositions described herein include, but are not limited to, carcinoma, lymphoma, blastoma, sarcoma, and leukemia. Examples of cancers that can be treated by compositions described herein include, but are not limited to, squamous cell cancer, lung cancer (including small cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, melanoma, endometrical or uterine carcinoma, salivary gland carcinoma, kidney or renal cancer, liver cancer, prostate cancer, vulval cancer, thyroid cancer, hepatic carcinoma, head and neck cancer, colorectal cancer, rectal cancer, soft-tissue sarcoma, Kaposi's sarcoma, B-cell lymphoma (including low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's macroglobulinemia), chronic lymphocytic leukemia (CLL), acute lymphoblastic leukemia (ALL), myeloma, Hairy cell leukemia, chronic myeloblastic leukemia, and post-transplant lymphoproliferative disorder (PTLD), as well as abnormal vascular proliferation associated with phakomatoses, edema (such as that associated with brain tumors), and Meigs' syndrome. In some embodiments, there is provided a method of treating metastatic cancer (that is, cancer that has metastasized from the primary tumor). In some embodiments, there is provided a method of reducing cell proliferation and/or cell migration. In some embodiments, there is provided a method of treating hyperplasia.

In some embodiments, there are provided methods of treating cancer at advanced stage(s). In some embodiments, there are provided methods of treating breast cancer (which may be HER2 positive or HER2 negative), including, for example, advanced breast cancer, stage IV breast cancer, locally advanced breast cancer, and metastatic breast cancer. In some embodiments, the cancer is lung cancer, including, for example, non-small cell lung cancer (NSCLC, such as advanced NSCLC), small cell lung cancer (SCLC, such as advanced SCLC), and advanced solid tumor malignancy in the lung. In some embodiments, the cancer is ovarian cancer, head and neck cancer, gastric malignancies, melanoma (including metastatic melanoma), colorectal cancer, pancreatic cancer, and solid tumors (such as advanced solid tumors). In some embodiments, the cancer is any of (and in some embodiments selected from the group consisting of) breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, gliomas, glioblastomas, neuroblastomas, and multiple myeloma. In some embodiments, the cancer is a solid tumor. In some embodiments, the cancer is any of (in some embodiments, selected from the group consisting of) prostate cancer, colon cancer, breast cancer, head and neck cancer, pancreatic cancer, lung cancer, and ovarian cancer.

Individuals suitable for receiving these compositions depend on the nature of the therapeutic agent, as well as the disease/condition/disorder to be treated and/or prevented. Accordingly, the terms "individual" and "subject" include any of vertebrates, mammals, and humans depending on intended suitable use. In some embodiments, the individual is a mammal. In some embodiments, the individual is any one or more of human, bovine, equine, feline, canine, rodent, or primate. In some embodiments, the individual is a human.

In further embodiments, the invention provides a method of treating carcinoma (such as colon carcinoma) in an individual, wherein the method comprises administering to the individual a composition comprising an effective amount of phospholipid-coated therapeutic agent nanoparticle.

The compositions described herein can be administered alone or in combination with other pharmaceutical agents, including poorly water soluble pharmaceutical agents. For example, when the composition comprises a taxane (such as paclitaxel), it can be co-administered with one or more other chemotherapeutic agents including, but are not limited to, carboplatin, Navelbine (vinorelbine), anthracycline (Doxil), lapatinib (GW57016), Herceptin, gemcitabine (Gemzar), capecitabine (Xeloda), alimta, cisplatin, 5-fluorouracil, epirubicin, cyclophosphamide, avastin, Velcade. In some embodiments, the taxane composition is co-administered with a chemotherapeutic agent selected from the group consisting of antimetabolites (including nucleoside analogs), platinum-based agents, alkylating agents, tyrosine kinase inhibitors, anthracycline antibiotics, vinca alkloids, proteasome inhibitors, macrolides, and topoisomerase inhibitors. These other pharmaceutical agents can be present in the same composition as the drug (such as taxane), or in a separate composition that is administered simultaneously or sequentially with the drug (such as taxane)-containing composition.

The dose of the composition of the invention administered to an individual will vary with the particular composition, the method of administration, and the particular disease being treated. The dose is sufficient to effect a desirable response, such as a therapeutic or prophylactic response against a particular disease or condition. For example, the dosage of representative therapeutic agents (e.g., paclitaxel) administered can be about 1 to about 300 mg/m$^2$, including for example about 10 to about 300 mg/m$^2$, about 30 to about 200 mg/m$^2$, and about 70 to about 150 mg/m$^2$. Typically, the dosage of a therapeutic agent (e.g., paclitaxel) in the composition can be in the range of about 50 to about 200 mg/m$^2$ when given on a 3 week schedule, or about 10 to about 100 mg/m$^2$ when given on a weekly schedule. In addition, if given in a metronomic regimen (e.g., daily or a few times per week), the dosage may be in the range of about 1-50 mg/m$^2$.

Dosing frequency for the compositions of the invention includes, but is not limited to, at least about any of once every three weeks, once every two weeks, once a week, twice a week, three times a week, four times a week, five times a week, six times a week, or daily. In some embodiments, the interval between each administration is less than about a week, such as less than about any of 6, 5, 4, 3, 2, or 1 day. In some embodiments, the interval between each administration is constant. For example, the administration can be carried out daily, every two days, every three days, every four days, every five days, or weekly. In some embodiments, the administration can be carried out twice daily, three times daily, or more frequent.

The administration of the compositions of the invention can be extended over an extended period of time, such as from about a month up to about three years. For example, the dosing can be extended over a period of any of about 2, 3, 4, 5, 6, 7, 8, 9, 10, 11, 12, 18, 24, 30, and 36 months. In some embodiments, there is no break in the dosing schedule. In some embodiments, the interval between each administration is no more than about a week.

The compositions described herein can be administered to an individual via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, and transdermal. In certain embodiments, the compositions are administered by any acceptable route including, but not limited to, orally, intramuscularly, transdermally, and intravenously.

When preparing the compositions for injection, particularly for intravenous delivery, the continuous phase preferably comprises an aqueous solution of tonicity modifiers, buffered to a pH range of about 5 to about 8.5. The pH may also be below 7 or below 6. In some embodiments, the pH of the composition is no less than about 6, including for example no less than about any of 6.5, 7, or 8 (such as about 7.5 or 8).

The nanoparticles of this invention can be enclosed in a hard or soft capsule, can be compressed into tablets, or can be incorporated with beverages or food or otherwise incorporated into the diet. Capsules can be formulated by mixing the nanoparticles with an inert pharmaceutical diluent and inserting the mixture into a hard gelatin capsule of the appropriate size. If soft capsules are desired, a slurry of the nanoparticles with an acceptable vegetable oil, light petroleum or other inert oil can be encapsulated by machine into a gelatin capsule.

In the practice of the methods of use, the invention provides methods of reducing side effects associated with administration of a therapeutic agent to a human, comprising administering to a human a pharmaceutical composition comprising the phospholipid-coated therapeutic agent nanoparticle. For example, the invention provides methods of reducing various side effects associated with administration of the therapeutic agent, including, but not limited to, myelosuppression, neurotoxicity, hypersensitivity, inflammation, venous irritation, phlebitis, pain, skin irritation, peripheral neuropathy, neutropenic fever, anaphylactic reaction, hematologic toxicity, and cerebral or neurologic toxicity, and combinations thereof. In some embodiments, there is provided a method of reducing hypersensitivity reactions associated with administration of the therapeutic agent, including, for example, severe skin rashes, hives, flushing, dyspnea, tachycardia, and others.

Methods of Making Phospholipid-Coated Therapeutic Agent Nanoparticles

In another aspect, the invention provides methods for making the phospholipid-coated therapeutic agent nanoparticles.

In certain embodiments, the methods for the formation of nanoparticles of the invention include preparation under conditions of high shear forces (e.g., sonication, high pressure homogenization, or the like). Representative methods for forming nanoparticles under high shear force conditions are described in U.S. Pat. Nos. 5,916,596; 6,506,405; and 6,537,579, incorporated herein by reference.

Briefly, in certain embodiments, the therapeutic agent is dissolved in an organic solvent to provide a solution that is combined with an aqueous phospholipid solution to provide a mixture. The mixture is subjected to high pressure homogenization. Post-homogenization to the desired level, the organic solvent is removed by evaporation to provide an aqueous dispersion. The dispersion obtained can be further lyophilized to provide a particulate solid.

Suitable organic solvents include solvents in which the therapeutic agent is soluble, that are miscible with aqueous solution, and that can be removed by evaporation at reasonable temperature and pressure. Representative useful solvents include ketones, esters, ethers, chlorinated solvents, and other solvents known in the art. For example, the organic solvent can be methylene chloride or chloroform/ethanol (for example, with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:1).

Pharmaceutically acceptable excipients can also be added to the composition. Suitable pharmaceutically acceptable excipients include solutions, emulsions, or suspensions.

Other emulsion or nanoparticle formulations may also be prepared. An emulsion is formed by homogenization under high pressure and high shear forces. Such homogenization is conveniently carried out in a high-pressure homogenizer, typically operated at pressures in the range of about 3,000 up to 30,000 psi. Preferably, such processes are carried out at pressures in the range of about 6,000 up to 25,000 psi. The resulting emulsion comprises very small nanodroplets of the non-aqueous solvent containing the dissolved therapeutic agent and very small nanodroplets of the phospholipid. Acceptable methods of homogenization include processes imparting high shear and cavitation such as, for example, high-pressure homogenization, high shear mixers, sonication, high shear impellers and the like.

Colloidal systems prepared in accordance with the present invention can be further converted into powder form by removal of the water (e.g., lyophilization) at a suitable temperature-time profile. The lyophilized product (e.g., particulate powder) is readily reconstituted by addition of water, saline or buffer, without the need to use conventional cryoprotectants such as mannitol, sucrose, glycine and the like. While not required, it is of course understood that conventional cryoprotectants can be added to the pharmaceutical compositions if so desired.

In one embodiment, the nanoparticles are prepared by microfluidization-solvent evaporation, as described in Example 1.

In another embodiment, the nanoparticles are prepared by thin-film hydration, as described in Example 2. Briefly, in this method, phospholipids and paclitaxel were dissolved in ethanol and subjected to rotary evaporation until a thin film was formed and all the solvents were evaporated. The film was then hydrated using deionized (DI) water to produce paclitaxel-loaded phospholipid nanoparticles.

The methods of the invention include methods of making pharmaceutical compositions comprising combining any of the compositions described herein with a pharmaceutically acceptable excipient.

In a further aspect, the invention provides use of the compositions described herein in the manufacture of a medicament. Particularly, the manufacture of a medicament for use in the treatment of conditions described herein. Further, the pharmaceutical composition thereof described herein, are also intended for use in the manufacture of a medicament for use in treatment of the conditions and, in accordance with the methods, described herein.

Representative Nanoparticle: Phospholipid-Coated Paclitaxel Nanoparticle

The following is a description of a representative nanoparticle of the invention, a phospholipid-coated paclitaxel nanoparticle.

In one embodiment, the present invention provides a phospholipid-coated paclitaxel nanoparticle formulation that utilizes phospholipids rather than either a natural polymer (Abraxane®) or a chemical polymer (Cynviloq®) as the next generation Abraxane®. See FIG. 1.

The effect of lipid composition and methods of preparation on drug loading and physical stability of paclitaxel-loaded lipid-coated nanoparticle formulation were evaluated.

The nanoparticles were prepared by two methods: microfludization-solvent evaporation and thin film-hydration methods. The formulation parameters included the type of phospholipid, phospholipid fatty acid chain length, the combination of phospholipid and lysophospholipid, the saturated-unsaturated phospholipid ratio, and the drug-phospholipid ratio. The process parameters such as microfludization pressure, number of microfludization cycles, and temperature of water for hydration were studied and their impact on drug loading, particle size, and physical stability were evaluated.

The short-term stability evaluation of nanoparticles prepared with different phospholipid ratios demonstrated that 4:1 as the optimum phospholipid-lysophospholipid ratio to achieve a loading of more than 60% paclitaxel with particle size of approximately 200 nm. The nanoparticle size increased with an increase of carbon chain lengths in the fatty acid, but no significant trends were observed for drug loading with changes in microfluidization pressure or number of cycles. The optimization of phospholipid composition, phospholipid types and process parameters led to a physically stable paclitaxel-loaded phospholipid-coated nanoparticle formulation that maintains size, charge, and integrity during storage.

The phospholipid-coated paclitaxel (PTX) nanoparticles (NPs) include biodegradable and biocompatible components such as phospholipid (PL), lyso-phospholipid (lyso-PL), and cholesterol. The extent of PTX loading in the phospholipid-coated NPs and the stability of such NPs are dependent on the nature, type, and concentration of phospholipids; method of preparation; and drug-lipid interaction that is determined by the drug-lipid ratio.

The factors influencing particle size, drug loading, and the physical stability of phospholipid-coated PTX NPs were determined.

Figure 2:
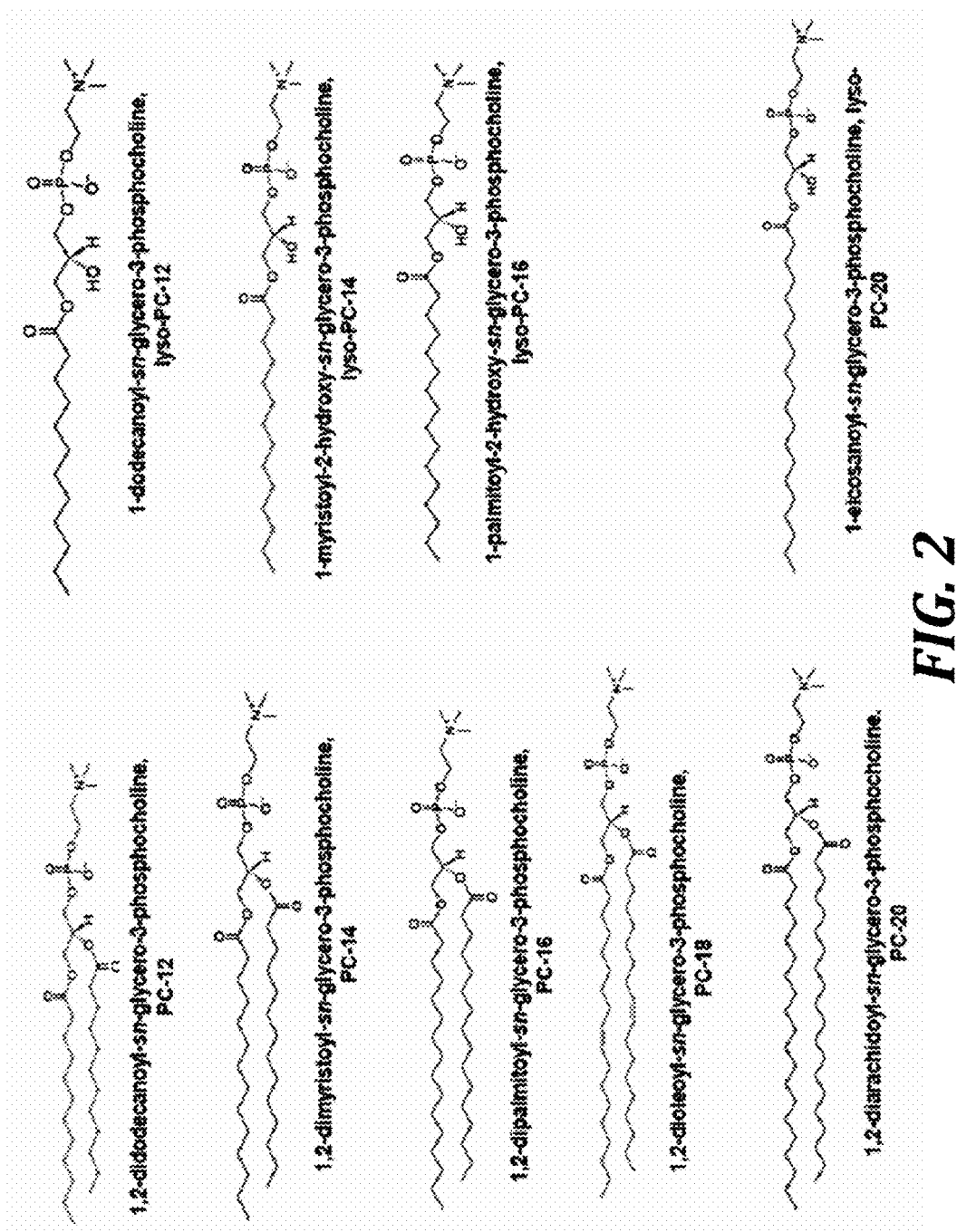
FIG. 2 schematically illustrates the chemical structures of phospholipids (phosphatidylcholines and lyso-phosphatidylcholines) useful in making representative phospholipid-coated therapeutic agent nanoparticles of the invention.

Combinative Formulation of PLs and Lyso-PLs by Microfluidization-Solvent Evaporation (Method 1) and Thin-Film Hydration (Method 2) Methods Two distinct PLs and lyso-PLs with different chain lengths and with significant phase transition temperature differences between the lipid in the combination were used to prepare PTX-NPs stabilized with the PLs. Molecular structures of the lipids used for the studies are shown in FIG. 2. The physical properties of the PLs and lyso-PLs are shown in Table 1. A series of combinations of PTX and lyso-PLs were investigated to develop a stable lipid-coated NP formulation for PTX.

TABLE 1

Physical properties of phospholipids and lyso-phospholipids used for the preparation of PTX-NPs.

| Name of lipid | MW | Transition Temp. (° C.) | CMC |
|---|---|---|---|
| PC-12 | 621.8 | −2 | 90.0 nM |
| lyso-PC-12 | 439.5 | NA | 0.4-0.9 mM |
| PC-14 | 677.933 | 24 | 6 nM |
| lyso-PC-14 | 467.57 | NA | 0.043-0.090 mM |
| PC 16 | 734.039 | 41 | 0.46 nM |
| Lyso-PC-16 | 495.63 | NA | 4-8.3 μM |
| PC-18 (unsaturated) | 786.113 | −17 | NA |
| PC-20 | 846.252 | 66 | NA |
| lyso-PC-20 | 551.7 | NA | NA |

Observations:
Transition temp. of the phosphatidylcholine (PC) increases with increase in length of carbon chain in the PC;
CMC of PC and lyso-PC decreases with increase in carbon chain length;
However, CMC of lyso-PC is much higher than that of corresponding (same carbon chain length) PC.

As shown in Table 2, microfluidization-solvent evaporation method in general produced particles of smaller size than thin-film hydration method. PLs or lyso-PLs alone did not produce smaller particles of size about 200 nm in either method.

TABLE 2

PTX-NPs Prepared by Microfluidization-Solvent Evaporation Method and Thin-film Hydration Method.

| Method of preparation | Amt. of PTX, Mg | Phospholipid constituents | | | | Size (Zav), nM | Polydispersity Index (PDI) |
|---|---|---|---|---|---|---|---|
| | | PC Name | Mg | lyso-PC Name | Mg | | |
| Microfluidization-solvent evaporation method | 10 | PC-12 | 50 | NA | NA | 401 | 0.9 |
| | | NA | NA | lyso-PC-20 | 50 | 2637 | 1.0 |
| | | NA | NA | lyso-PC-12 | 50 | 2349 | 1.0 |
| | | PC-12 | 40 | lyso-PC-12 | 10 | 206 | 0.4 |
| | | PC-12 | 40 | lyso-PC-20 | 10 | 325 | 0.7 |
| | | PC-20 | 40 | lyso-PC-12 | 10 | 3042 | 0.4 |
| | | PC-20 | 40 | lyso-PC-20 | 10 | 35630 | 0.3 |
| | | PC-12 | 10 | lyso-PC-12 | 40 | 1767 | 0.2 |
| | | PC-12 | 10 | lyso-PC-20 | 40 | 308 | 1.0 |
| Thin-film hydration | 10 | PC-12 | 50 | NA | NA | 1427 | 0.3 |
| | | NA | NA | lyso-PC-20 | 50 | 517 | 0.6 |
| | | NA | NA | lyso-PC-12 | 50 | 7325 | 0.5 |
| | | PC-12 | 40 | lyso-PC-12 | 10 | 1319 | 0.8 |
| | | PC-12 | 40 | lyso-PC-20 | 10 | 1166 | 0.5 |
| | | PC-20 | 40 | lyso-PC-12 | 10 | 10210 | 0.7 |
| | | PC-20 | 40 | lyso-PC-20 | 10 | 24670 | 1.0 |
| | | PC-12 | 10 | lyso-PC-12 | 40 | 3023 | 1.0 |
| | | PC-12 | 10 | lyso-PC-20 | 40 | 9546 | 1.0 |

Observations:
Microfluidization-solvent evaporation method in general produced particles smaller than thin-film hydration method;
Combination of PL and lyso-PL produced smaller size particle of 200-300 nm by microfluidization-evaporation method;
Phospholipids or lyso-PLs alone did not produce smaller particles of size ~200 nm in either methods.

Effect of Carbon Chain Length in PC and Lyso-PC on PTX Loading

The particle size and entrapment efficiency of PTX in PC and lyso-PC combination by method 1 is shown in Table 3. The combination of PC-12 and lyso-PC-12 produced smallest size particles with highest loading of PTX. The combination of phosphatidylcholine and cholesterol had very poor entrapment efficiency of PTX.

TABLE 3

PTX-NPs prepared in different combinations of PLs, lyso-PLs and cholesterol by microfluidization solvent evaporation method.

| Phospholipid | | lyso-phospholipid/ cholesterol | | PTX (Mg) | Particle size ($Z_{av}$) of 0.2 μm formulation | Entrapment Efficiency (%) |
|---|---|---|---|---|---|---|
| Name | Mg | Name | Mg | | | |
| PC-12 | 40 | Lyso-PC-12 | 10 | 10 | 95 | 45.0 |
| PC-14 | 40 | Lyso-PC-14 | 10 | 10 | 169.8 | 3.91 |
| PC-16 | 40 | Lyso-PC-16 | 10 | 10 | 377.3 | 6.69 |
| PC-12 | 40 | Lyso-PC-14 | 10 | 10 | 91.4 | 11.3 |
| PC-12 | 40 | Lyso-PC-16 | 10 | 10 | 72.89 | 9.46 |
| PC-12 | 40 | Cholesterol | 10 | 10 | 238.6 | Too low |
| PC-14 | 40 | Cholesterol | 10 | 10 | 173.6 | Too low |
| PC-16 | 40 | Cholesterol | 10 | 10 | 158.3 | Too low |
| PC-12 | 40 | Cholesterol Lyso 12 | 5 5 | 10 | 128 | 7.49 |

Observations:
The combination of PC-12 and lyso-PC-12 produced smallest size particles with highest loading of PTX;
The combination phosphocholine and cholesterol had very poor entrapment efficiency of PTX.

FIG. 3 is the particle size distribution graph by dynamic laser light scattering for the optimized formulation of PTX-NP formulation stabilized by combination of PC-12 and lyso-PC-12. Referring to FIG. 3, there are very few large particles in the unfiltered formulation. The formulation was easily filterable through 0.2 µm filter and the filtered NP formulation of PTX has monomodal size distribution with a polydispersity index of 0.1. The $Z_{av}$ of the optimized formulation was about 100 nm.

Effect of Extrusion Cycles on Particle Size and Drug Loading

The number of extrusion cycles used in the preparation of lipid-coated PTX-NPs can affect drug loading depending upon the number of extrusion cycles. The effects of the number of extrusion cycles on particle size and entrapment efficiency are shown in FIG. 4. The results are shown for the drug-lipid ratio of 1:5 and the PC-12-lyso-PC-12 of 80:20. The size of the NPs was unchanged with increasing number of extrusion cycles. There was significant increase in the entrapment of PTX up to twelve extrusion cycles.

Optimization of PC-12 and Lyso-PC-12 Ratio

Figure 5:
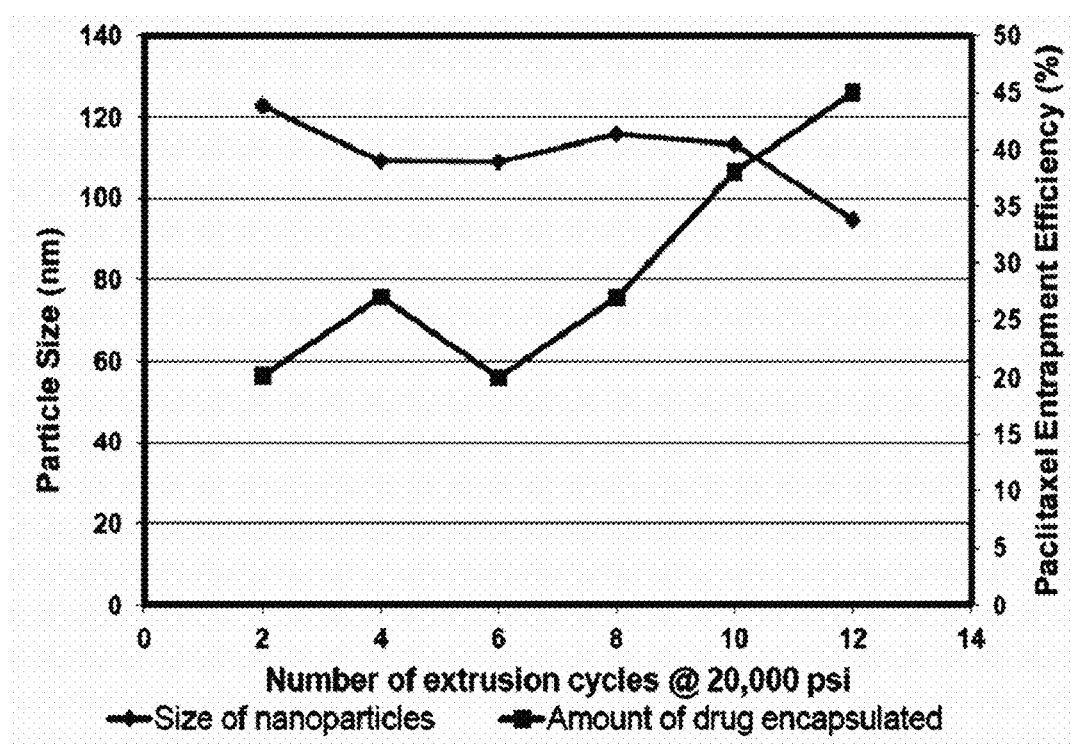
FIG. 5 compares the effect of the number of extrusion cycles on nanoparticle size and therapeutic agent entrapment efficiency for representative phospholipid-coated therapeutic agent (paclitaxel) nanoparticles of the invention prepared by a microfluidization-solvent evaporation method.
Figure 6:
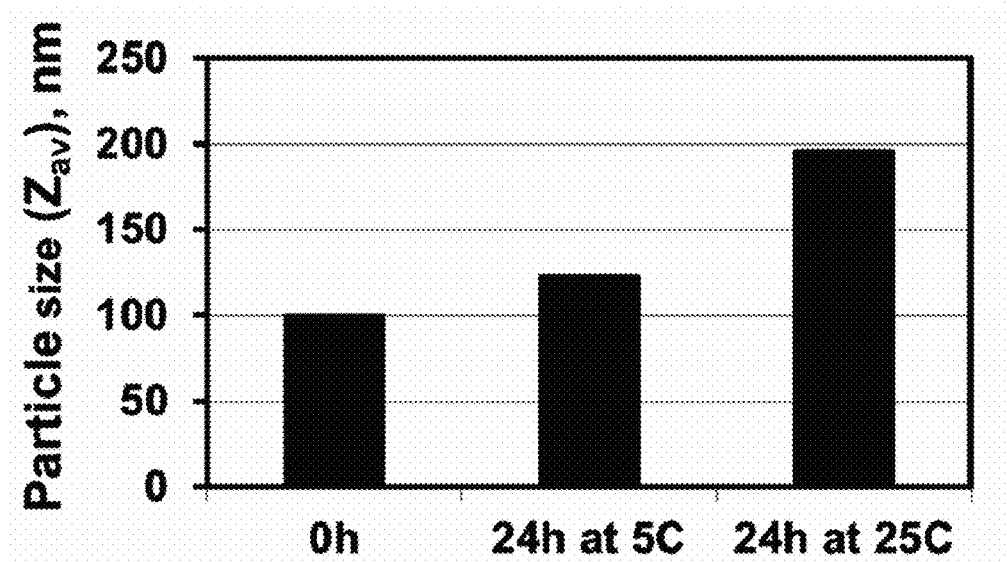
FIG. 6 compares particle size as a function of time for representative phospholipid-coated therapeutic agent (paclitaxel) nanoparticles of the invention.

The effect of PC and lyso-PC ratio on PTX loading under similar conditions of preparation is shown in FIG. 5. The maximum entrapment of PTX was obtained at the ratio of PC-12:lyso-PC-12 of 4:1. The particle size was smaller with increasing amount of lyso-PC-12. The smaller size particles at higher concentration of lyso-PC-12 could be due to micellar particles of lyso-PC-12 with no PTX loading.

The combination of PC-12 and lyso-PC-12 produced the smallest size PTX-NP. The greatest entrapment efficiency of 45% was achieved for the formulation with 12 passes. Addition of cholesterol in the formulation did not improve PTX loading. A ratio of 80:20 of PC-12:lyso-PC-12 was optimum for nanoparticle size, drug incorporation, and stability. The optimized formulation had a particle size about 100 nm. The optimized formulation is stable for 24 h at 4° C.

Injectable Phospholipid-Coated Nanoparticles Loaded with Paclitaxel

Composition, Method of Preparation, Electrochemical Characterization, and Dissolution Profiles Successful paclitaxel nanoparticles formulations include Abraxane (an albumin bound nanoparticle paclitaxel) and Genexol-PM® (a polymer bound nanoparticle paclitaxel). The development of Genexol-PM® was a significant step forward in manufacturing with utilization of a one pot synthesis technique using a biodegradable di-block copolymer composed of methoxy-poly(ethylene glycol)-poly(lactide) to form nanoparticles with paclitaxel containing hydrophobic core and a hydrophilic shell (See FIG. 1). However, clinical hypersensitivity and instability in serum/plasma remain problematic. The present invention provides a one-pot synthesis of paclitaxel nanoparticle formulations using phospholipids that retain the desired plasma instability of Abraxane and the phosphate buffered saline (PBS) stability of Genexol-PM®. Due to the use of naturally occurring phospholipids in the paclitaxel nanoparticles of the invention, hypersensitivity should not be an issue.

Nanoparticle synthesis was conducted using two methods: Method 1, microfluidization-solvent evaporation (similar to Abraxane® method); and Method 2, thin-film hydration (one-pot method similar to Genexol-PM® method). Briefly, in Method 2, phospholipids and paclitaxel were dissolved in ethanol and subjected to rotary evaporation until a thin film was formed and all the solvents were evaporated. The film was then hydrated using deionized (DI) water to produce paclitaxel-loaded phospholipid nanoparticles. Nanoparticle size and zeta potential were measured using a Malvern ZS DLS system. The formulations were subjected to serial filtration using 1.2 µm, 0.8 µm, 0.45 µm, and 0.2 µm syringe filters. The drug incorporation/loading in the phospholipid nanoparticles was measured using ELISA. Electrochemical properties of the formulation were measured using screen printed carbon nanotube electrodes from DropSens and a PGSTAT204 Autolab station from Metrohm. Testing for dissolution of nanoparticles in human plasma, 50 mg/mL human serum albumin (HSA) solution, PBS and DI water was performed by measuring nanoparticle size using dynamic light scattering.

A series of phospholipids and lyso-phospholipids were tested for assembly of paclitaxel nanoparticles.

FIG. 7 compares particle size (at t=0) and paclitaxel incorporation (%) for representative phospholipid-coated therapeutic agent (paclitaxel) nanoparticles of the invention prepared by microfluidization and thin film evaporation methods.

Figure 8:
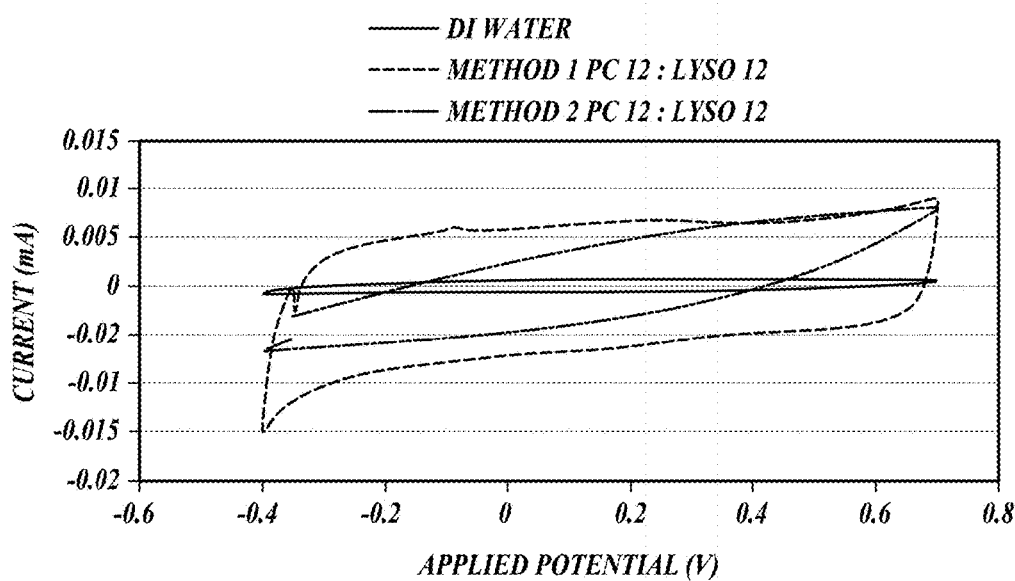
FIG. 8 compares electrochemical response (cyclic voltammetry: current (mA) v. applied potential (V)) for representative phospholipid-coated therapeutic agent (paclitaxel) nanoparticles of the invention (PC 12: Lyso 12) prepared by microfluidization and thin film evaporation methods.

The findings were as follows: short chain lipids such as PC 10 (1,2-didecanoyl-sn-glycero-3-phosphocholine), PC 12 (1,2-dilauroyl-sn-glycero-3-phosphocholine), Lyso PC 10 (1-decanoyl-2-hydroxy-sn-glycero-3-phosphocholine) and Lyso PC 12 (1-lauroyl-2-hydroxy-sn-glycero-3-phosphocholine) produced particles with good drug loading, optimal size, and stability. Method 2 produced nanoparticles with higher drug loading and higher stability as compared to Method 1. The electrochemical properties of formulations synthesized using Method 1 and Method 2 were different with one being weakly negatively charged and the other being weakly positively charged, probably due to the neutrality nature of PC and lyso-PC. Each formulation exhibited distinct cyclic voltammetry (CV) scan (FIG. 8). The difference in charge on the particles produced by two different methods is indicative of different organization of lipids around the particles produced by Method 1 and Method 2.

FIG. 8 compares electrochemical response (cyclic voltammetry: current (mA) v. applied potential (V)) for representative phospholipid-coated therapeutic agent (paclitaxel) nanoparticles of the invention (PC 12: Lyso 12) prepared by microfluidization and thin film evaporation methods.

The phospholipid nanoparticles produced using Method 2 (LM-101) rapidly disintegrated in human plasma showing that that these nanoparticles (FIG. 10C) have dissolution properties similar to Abraxane® (FIG. 10A) and Genexol-PM® (FIG. 10C). Like Genexol-PM®, the nanoparticles remained intact in deionized water and phosphate buffered saline (PBS) solution even at very low paclitaxel concentration (1-10 ug/ml). This property allows for LM-101 to be administered as PBS-diluted solution into peritoneal cavity for treatment of ovarian cancer or distilled into the bladder for treatment of bladder cancer. The results show that the high plasma/serum instability of Genexol-PM® was eliminated and that LM-101 acquired behavior similar to that of Abraxane® in serum/plasma. This allows LM-101 to be administered intravenously with pharmacokinetic properties of Abraxane® for the treatment of breast, lung, pancreatic, and melanoma cancers.

FIG. 9 compares dissolution of representative phospholipid-coated therapeutic agent (paclitaxel) nanoparticles of the invention in deionized water (DI), phosphate buffered saline (PBS), and human plasma (50 mg/mL human serum albumin/PBS) showing particle size (nm) as a function of paclitaxel concentration (µg/mL).

Figure 10A:
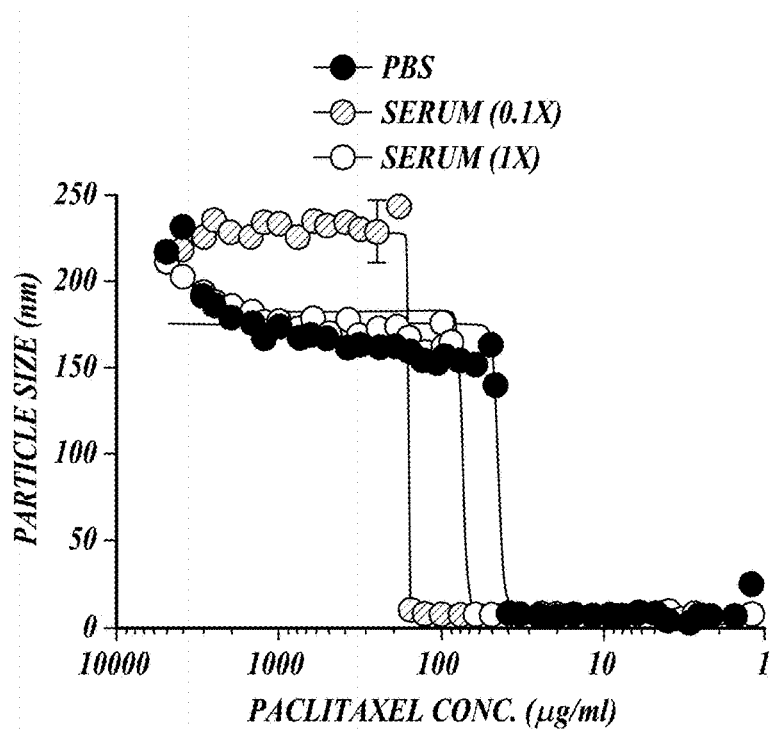
FIGS. 10A, 10B, and 10C compare dissolution of Abraxane® nanoparticles (10A), Genexol-PM® nanoparticles (10B), and representative phospholipid-coated therapeutic agent (paclitaxel) nanoparticles of the invention (10C) in deionized water (water), phosphate buffered saline (PBS), serum (0.1×: 5 mg/mL HSA/PBS), serum (1.0×: 50 mg/mL HSA/PBS), simulated plasma (50 mg/mL HSA/PBS), and plasma showing particle size (nm) as a function of paclitaxel concentration (μg/mL).
Figure 10B:
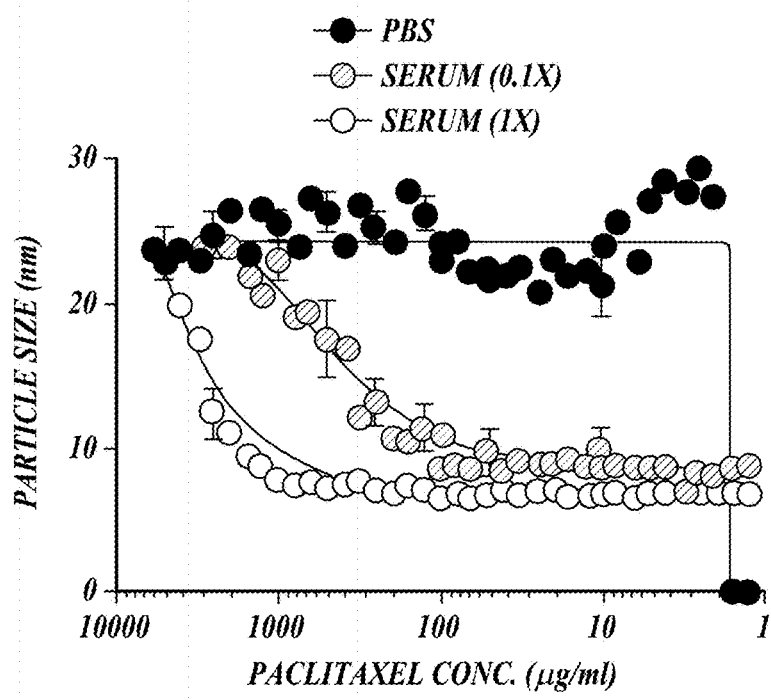
Figure 10C:
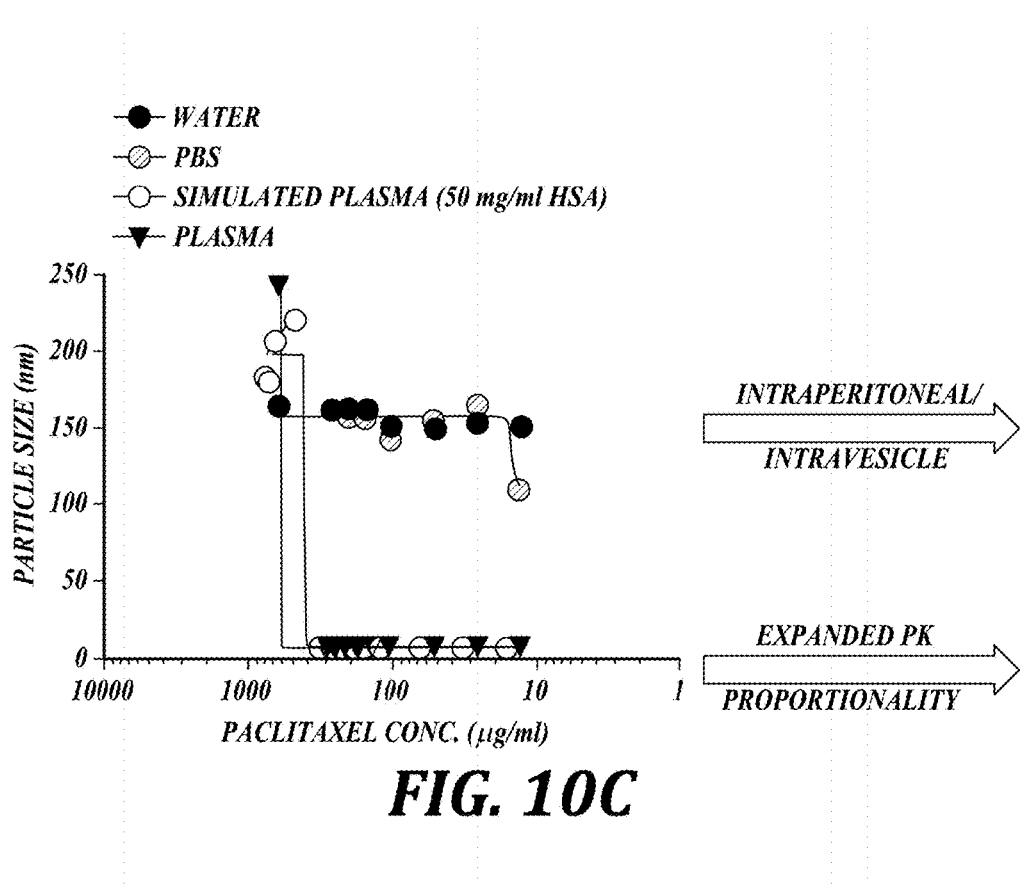

FIGS. 10A, 10B, and 10C compare dissolution of Abraxane® nanoparticles (10A), Genexol-PM® nanoparticles (10B), and representative phospholipid-coated therapeutic agent (paclitaxel) nanoparticles of the invention (10C) in deionized water (water), phosphate buffered saline (PBS), serum (0.1×: 5 mg/mL HSA/PBS), serum (1.0×: 50 mg/mL HSA/PBS), simulated plasma (50 mg/mL HSA/PBS), and plasma showing particle size (nm) as a function of paclitaxel concentration (µg/mL).

Stability of Injectable Phospholipid Nanoparticles Loaded with Paclitaxel: Influence of Lipid Composition, Drug Concentration, Storage Temperature, Lyophilization, and Additive Paclitaxel is one of the most effective chemotherapeutic drugs for solid tumors including breast, lung and ovarian cancers. Paclitaxel has been formulated as a nanoparticle formulation, Abraxane®, to improve its solubility (0.35-0.7 µg/mL) and to avoid the use of harmful solvents like cremophor EL. A next generation Abraxane has been reported: Cynviloq®, a polymeric micelle paclitaxel formulation that uses a chemical polymer rather than a biological polymer to stabilize the nanoparticle. The present invention provides the use of phospholipids rather than the Cynviloq® chemical polymer for the creation of the next generation Abraxane®.

The effect of lipid composition on drug loading and physical stability of paclitaxel-loaded lipid-coated nanoparticle formulations was evaluated before and after lyophilization. The nanoparticles were prepared by microfluidization-solvent evaporation and thin-film evaporation methods. The formulation parameters included type of phospholipids, phospholipid fatty acid chain length, ratio of phospholipid and lysophospholipid combination, and drug-phospholipid ratio. The process parameters such as microfluidization pressure and number of microfluidization cycles were studied and their impact on drug loading, particle size, and physical stability were evaluated.

The short-term stability evaluation of nanoparticles prepared with different phospholipid ratios demonstrated that 4:1 as the optimum phospholipid-lysophospholipid ratio to achieve a loading of more than 80% paclitaxel with particle size of approximately 200 nm. The nanoparticle size increased with an increase of carbon chain length of the phospholipid fatty acid, but no significant trends were observed for drug loading with changes in microfluidization pressure or number of cycles. The stability of the formulation was evaluated at different temperatures before and after lyophilization. The optimization of phospholipid composition, drug-lipid ratio, process parameters, and additives for stability on lyophilization led to a physically stable paclitaxel-loaded phospholipid-coated nanoparticulate formulation that maintains size, charge, and particulate integrity during storage.

The phospholipid-coated paclitaxel loaded nanoparticles consisted of biodegradable and biocompatible components such as phospholipid, lyso-phospholipid, and cholesterol. The extent of paclitaxel loading in the phospholipid-coated nanoparticles and the stability of these nanoparticles was determined to be dependent on (i) the nature, type and concentration of phospholipids, (ii) the method of preparation, and (iii) the drug-lipid interaction that is determined by the drug-lipid ratio.

The following describes the optimization of factors influencing particle size, drug loading, and the physical stability of phospholipid-coated PTX-loaded NPs before and after lyophilization.

The paclitaxel-phospholipid nanoparticles (PTX-NPs) were prepared by two methods: microfluidization-solvent evaporation and thin-film hydration methods.

Method 1: Microfluidization-Solvent Evaporation Method.

The paclitaxel-phospholipid nanoparticles (PTX-NPs) were prepared by LV1 low volume Microfluidizer® processor microfluidization. The organic solvent containing paclitaxel and phospholipids were added to an aqueous phase and the emulsion was run through the microfluidizer to obtain nanoemulsion. The solvent from the nanoemulsion was removed by rotoevaporation to obtain a nanosuspension of paclitaxel.

Method 2: Thin-Film Hydration Method.

The phospholipid film was prepared by dissolving paclitaxel and phospholipids in ethanol. The dry film was hydrated with water for visual, microscopic, size, and loading efficiency measurements of the resulting unfiltered formulation.

NP Size Measurement.

The particle size and the particle size measurements were carried out using Zetasizer Nano-ZS and the $Z_{av}$ hydrodynamic diameter of the samples was determined by cumulative analysis. The particle size and particle size distribution by intensity were measured by photon correlation spectroscopy (PCS)) using dynamic laser light scattering (4 mW He—Ne laser with a fixed wavelength of 633 nm, 173° backscatter at 25° C.) in 10 mm diameter cells.

Combinative Formulation of Phospholipids (PLs) and Lysophospholipids (Lyso-PLs) Prepared by Microfluidization-Solvent Evaporation (Method 1) and Thin-Film Hydration (Method 2) Methods.

Two distinct PLs and Lyso-PLs with different chain lengths and with significant phase transition temperature differences were used in the combination to prepare paclitaxel nanoparticles (PTX-NPs) stabilized with the phospholipids. Molecular structures of the lipids used for the studies are shown in FIG. 2. The physical properties of the PLs (PC-12-PC-20) and Lyso-PLs (lyso-PC-12-lyso-PC-20) are shown in Table 1 above.

A series of combinations of PLs and Lyso-PLs were investigated to develop a stable lipid-coated nanoparticle formulation for paclitaxel.

Figure 11:
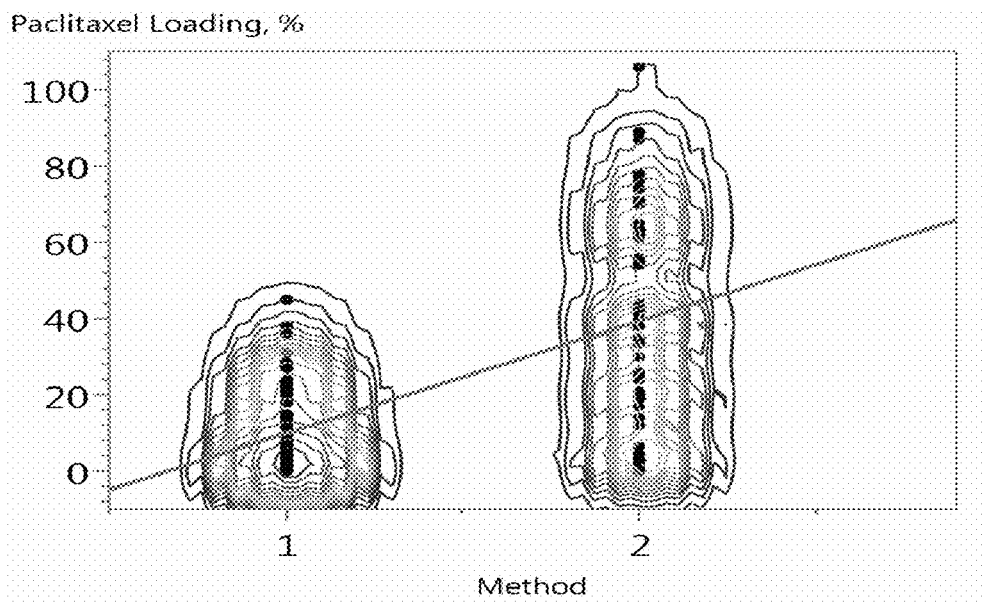
FIG. 11 compares paclitaxel loading (%) for representative phospholipid-coated therapeutic agent (paclitaxel) nanoparticles of the invention, PC-coated paclitaxel nanoparticle, prepared by microfluidization-solvent evaporation (Method 1) and thin film-hydration evaporation (Method 2) methods.

As shown in FIG. 11, thin-film hydration method in general produced particles of higher loading (up to 90%) than microfluidization-solvent evaporation method. PLs or lyso-PLs alone did not produce smaller particles of size about 200 nm in either method.

FIG. 11 compares paclitaxel loading (%) for representative phospholipid-coated therapeutic agent (paclitaxel) nanoparticles of the invention, PC-coated paclitaxel nanoparticle (LM-101), prepared by microfluidization-solvent evaporation (Method 1) and thin film-hydration evaporation (Method 2) methods.

Figure 12:
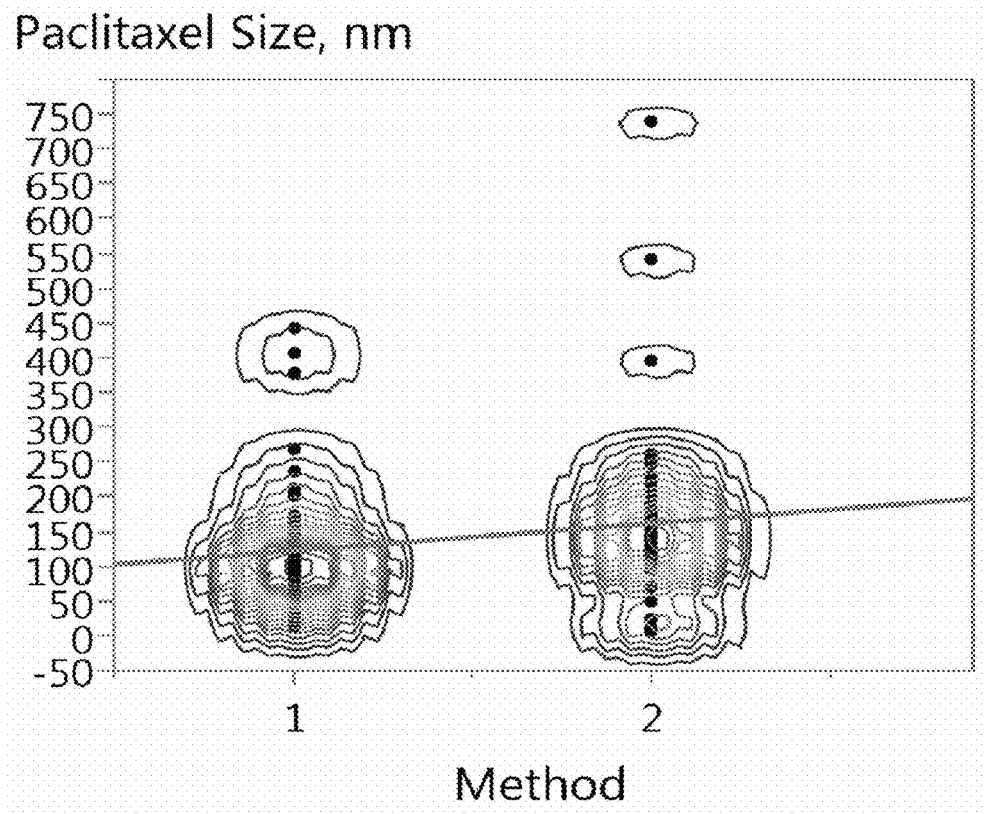
FIG. 12 compares particle size (nm) for representative phospholipid-coated therapeutic agent (paclitaxel) nanoparticles of the invention, PC-coated paclitaxel nanoparticle, prepared by microfluidization-solvent evaporation (Method 1) and thin film-hydration (Method 2) methods.

The combination of PL and lyso-PL produced smaller size particles of about 200 nm by either method (FIG. 12).

FIG. 12 compares particle size (nm) for representative phospholipid-coated therapeutic agent (paclitaxel) nanoparticles of the invention, PC-coated paclitaxel nanoparticle (LM-101), prepared by microfluidization-solvent evaporation (Method 1) and thin film-hydration (Method 2) methods.

Screening of Carbon Chain Length in PC and Lyso-PC and Temperature of Rehydration for PTX Loading.

The entrapment efficiency of paclitaxel in the PC:Lyso PC combination by Method 2 is shown in FIG. 13. The combination of PC-10 and Lyso-PC-10 produced with highest loading of paclitaxel in general.

FIG. 13 compares paclitaxel loading (%) for representative phospholipid-coated therapeutic agent (paclitaxel) nanoparticles of the invention as a function of PC carbon length (6-22) prepared by the thin film-hydration method (Method 2).

Figure 14:
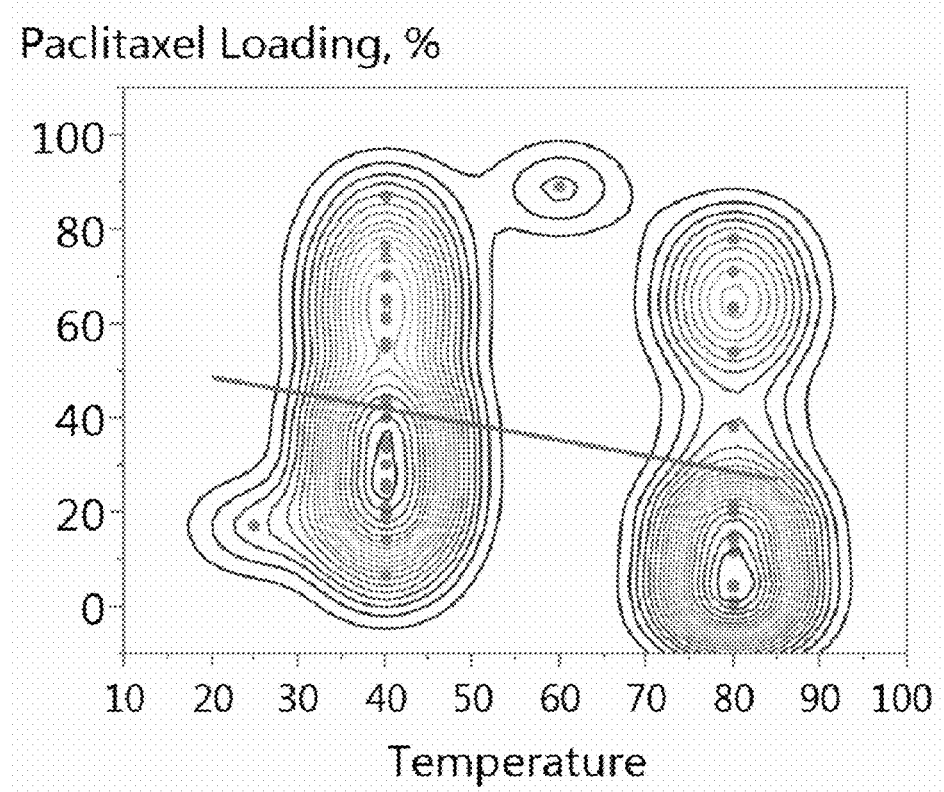
FIG. 14 compares paclitaxel loading (%) for representative phospholipid-coated therapeutic agent (paclitaxel) nanoparticles of the invention as a rehydration water temperature for nanoparticles prepared by the thin film-hydration method (Method 2).

The highest entrapment efficiency of paclitaxel of about 90% was obtained with water of temperature 40° C. for rehydration (FIG. 14).

FIG. 14 compares paclitaxel loading (%) for representative phospholipid-coated therapeutic agent (paclitaxel) nanoparticles of the invention as a rehydration water temperature for nanoparticles prepared by the thin film-hydration method (Method 2).

Screening of the Type and Amount of Lyoprotectants for Stabilization of Nanoparticles on Lyophilization.

Figure 15:
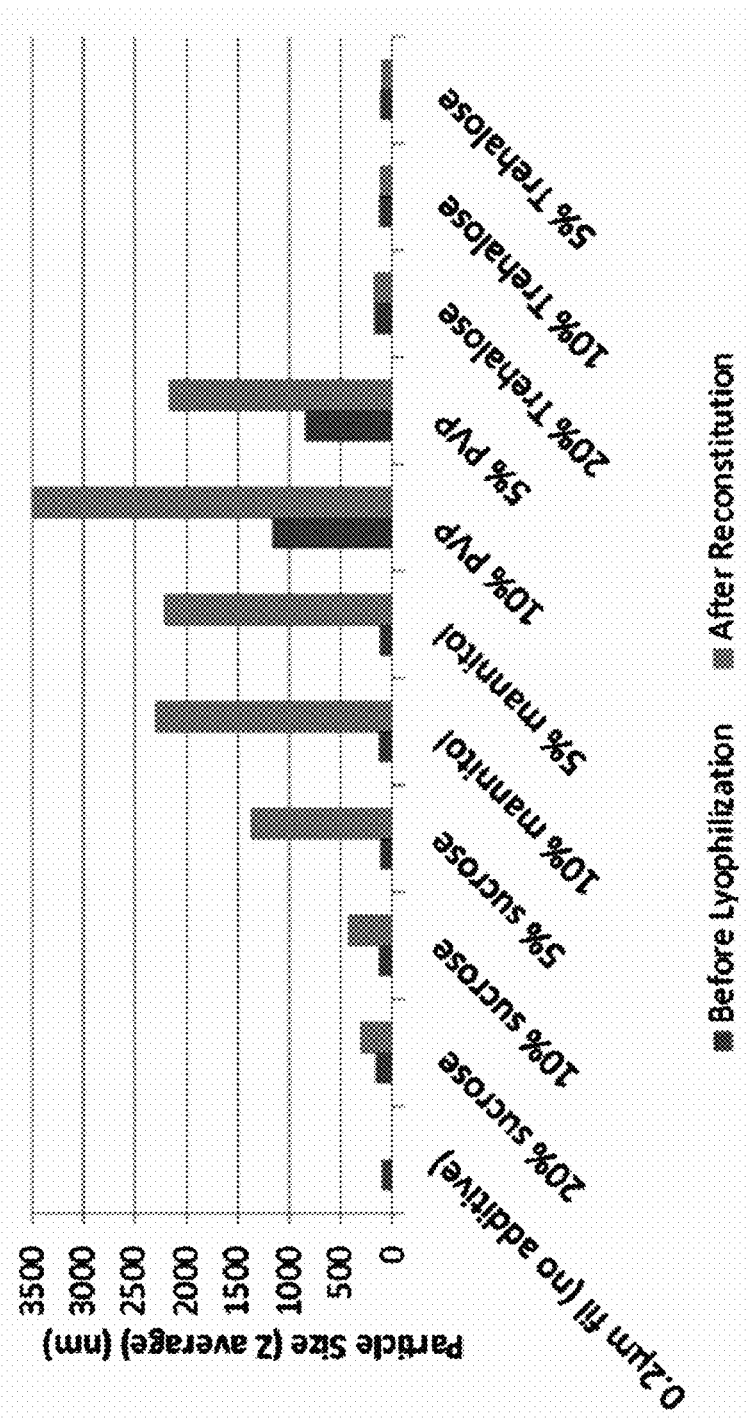
FIG. 15 compares particle size as a function of lyoprotectant and lyoprotectant amount for representative phospholipid-coated therapeutic agent (paclitaxel) nanoparticles of the invention, PC-coated paclitaxel nanoparticle manufactured by thin film-hydration method (LM-101), before lyophilization and after reconstitution.

The protective abilities of sucrose, mannitol, PVP, and trehalose as single lyoprotectants in different amounts were evaluated. Trehalose in amounts 5-20% were found to be best in stabilizing the particles on lyophilization as shown in FIG. 15. Trehalose was the best excipient as lyoprotectant to inhibit the growth of particles on lyophilization.

FIG. 15 compares particle size as a function of lyoprotectant and lyoprotectant amount for representative phospholipid-coated therapeutic agent (paclitaxel) nanoparticles of the invention, PC-coated paclitaxel nanoparticle manufactured by thin film-hydration method (LM-101), before lyophilization and after reconstitution.

Formulations with 5-10% trehalose were stable for 4 hours at room temperature after reconstitution (FIG. 16).

FIG. 16 compares particle size as a function of time (t=0 and 4 hr) after reconstitution with 3.2 mM histidine buffer at pH 5.5 for representative phospholipid-coated therapeutic agent (paclitaxel) nanoparticles of the invention, PS-coated paclitaxel nanoparticle manufactured by thin film-hydration method (LM-101).

As used herein, the term "about" and "substantially" refer to a variation of less than 10% from the object of the term.

The following examples are provided for the purpose of illustrating, not limiting, the invention.

EXAMPLES

Example 1

The Preparation of Representative Paclitaxel Nanoparticles by Microfluidization-Solvent Evaporation The PTX-phospholipid NPs were prepared by LV1 low volume Microfluidizer® processor (Microfluidics, Massachusetts, US) microfluidization. The organic solvent (ethanol:chloroform (9:1)) containing PTX and phospholipids were added to an aqueous phase (de-ionized water, DI) and the emulsion was run through the microfluidizer to provide a nanoemulsion. The solvent from the nanoemulsion was removed by rotary evaporation to provide a nanosuspension of phospholipid-coated PTX nanoparticles in the aqueous phase.

Nanoparticles were prepared by mixing together the organic and aqueous phase. Organic phase consisted of 40 mg of 12:0 PC (DLPC) 1,2-dilauroyl-sn-glycero-3-phosphocholine (Avanti Polar Lipids, Inc., Alabama, US), 10 mg of 12:0 lyso PC 1-lauroyl-2-hydroxy-sn-glycero-3-phosphocholine (Avanti Polar Lipids, Inc., Alabama, US) and 10 mg of paclitaxel (paclitaxel was from Tecoland Corporation, Irvine, Calif. (DMF No. 11909)) dissolved in 0.16 ml of ethanol:chloroform (9:1) solvent. The aqueous phase consists of 1.84 ml of DI water. The organic and aqueous phases were initially mixed using a homogenizer (VWR® 200 Homogenizer) for 1 minute to obtain micro sized particles or microemulsion. The micro-sized particles were further broken down to form nanoparticles using the LV1 microfluidizer. The formulation was pushed through 12 passes of the microfluidizer at a process pressure of 20,000 psi. The formulation was then immediately subjected to rotary evaporation at the following conditions (water bath temperature=40° C., chiller temperature=5° C., vacuum=25 mm Hg, rotation=280 rpm, flask size=250 ml). The evaporation was continues until all the solvent was removed and no bubbles could be further observed in the flask. The formulation was the diluted to a final volume of 10 ml using DI water.

The phospholipids used were all of research grade: 1,2-didodecanoyl-sn-glycero-3-phosphocholine (DLPC); 1,2-dimyristoyl-sn-glycero-3-phosphocholine (DMPC); 1,2-dipalmitoyl-sn-glycero-3-phosphocholine (DPPC); 1,2-dioleoyl-sn-glycero-3-phosphocholine (DOPC); 1,2-diarachidoyl-sn-glycero-3-phosphocholine (DAPC); 1-dodecanoyl-sn-glycero-3-phosphocholine (lyso-LPC); 1-myristoyl-2-hydroxy-sn-glycero-3-phospho-choline (lyso-MPC); 1-palmitoyl-2-hydroxy-sn-glycero-3-phosphocholine (LPC), 1-eicosanoyl-sn-glycero-3-phosphocholine (lyso-EPC) were purchased from Avanti Polar Lipids, Inc. (Alabama, US). Cholesterol was obtained from Sigma (St. Louis, Mo.). HPLC grade water and ethanol were obtained from Fisher Scientific (Fair Lawn, N.J.). HPLC grade chloroform was purchased from Acros Organics (Morris Plains, N.J.). All other chemicals and reagents were of analytical grade and used without further purification or characterization.

Example 2

The Preparation of Representative Paclitaxel Nanoparticles by Thin-Film Hydration A phospholipid film was prepared by dissolving PTX and phospholipids in ethanol. The dry film was hydrated with water for visual, microscopic, size and loading efficiency measurements of the resulting unfiltered formulation.

Organic phase consisted of 40 mg of 12:0 PC (DLPC) 1,2-dilauroyl-sn-glycero-3-phosphocholine (Avanti Polar Lipids, Inc., Alabama, US), 10 mg of 12:0 lyso PC 1-lauroyl-2-hydroxy-sn-glycero-3-phosphocholine (Avanti Polar Lipids, Inc., Alabama, US) and 10 mg of paclitaxel (paclitaxel was from Tecoland Corporation, Irvine, Calif. (DMF No. 11909)) dissolved in 10 ml of ethanol. Aqueous phase consists of 10 ml DI water. The two phases are mixed in a 250 ml evaporator flask. The solution is completely evaporated using a rotary evaporator at the following conditions: water bath temperature=28° C., pressure<2 mm Hg, chiller temperature=5° C., rotation speed=280 rpm, until a film is formed on the flask. The water bath temperature is then increased to 60° C. and residual ethanol is removed by evaporation for another 1 hour. 10 ml DI water heated to 60°

C. is then added to the flask and the film is rehydrated with continuous stirring using a magnetic stirrer for 30 minutes.

Example 3

Size and Zeta Potential Measurement of Representative Paclitaxel Nanoparticles

The particle size and the particle size measurements were carried out using Zetasizer Nano-ZS (Malvern Instruments Ltd, Worcestershire, UK) and the $Z_{av}$ hydrodynamic diameter of the samples was determined by cumulative analysis. The particle size and particle size distribution by intensity were measured by photon correlation spectroscopy (PCS) using dynamic laser light scattering (4 mW He—Ne laser with a fixed wavelength of 633 nm, 173° backscatter at 25° C.) in 10 mm diameter cells. The $Z_{av}$ of the particle size, also known as cumulants mean, is defined as harmonic intensity average particle diameter. All measurements were done with six runs. Zeta potential (surface charge) determinations of the NPs in water were based on the electrophoretic mobility of the particles using folded capillary cells in automatic mode of measurement duration using Zetasizer Nano-ZS. The measurements were performed by the laser scattering method using Smoluchowski model (Laser Doppler Microelectrophoresis, He—Ne laser 633 nm at 25° C.). All measurements were done with six runs.

While the preferred embodiment of the invention has been illustrated and described, it will be appreciated that various changes can be made therein without departing from the spirit and scope of the invention.

The invention claimed is:

1. A phospholipid-coated therapeutic agent nanoparticle, comprising a particulate therapeutic agent coated with one or more phospholipids,
wherein the nanoparticle is stable in aqueous delivery vehicles for administration and releases the therapeutic agent substantially instantaneously upon exposure to or contact with a physiological fluid.

2. A phospholipid-coated therapeutic agent nanoparticle, comprising a particulate therapeutic agent coated with one or more phospholipids,
wherein the nanoparticle is substantially electronically neutral based on phospholipid composition, and
wherein the nanoparticle is stable in aqueous delivery vehicles for administration and releases the therapeutic agent substantially instantaneously upon exposure to or contact with a physiological fluid.

3. The nanoparticle of claim 1, wherein the one or more phospholipids is a diacylphospholipid selected from the group consisting of diacylphosphatidylcholines, diacylphosphatidylethanolamines, diacylphosphatidylglycerols, diacylphosphatidylserines, diacylphosphatidylinositols, diacylphosphatidic acids, and mixtures thereof.

4. The nanoparticle of claim 3, wherein the diacylphospholipid is a phosphatidylcholine selected from the group consisting of distearoylphosphatidylcholine (DSPC), dioleoylphosphatidylcholine (DOPC), dipalmitoylphosphatidylcholine (DPPC), dilinoleoylphosphatidylcholine DLPC), palmitoyloleoylphosphatidylcholine (POPC), palmitoyllinoleoylphosphatidylcholine, stearoyllinoleoylphosphatidylcholine stearoyloleoylphosphatidylcholine, stearoylarachidoylphosphatidylcholine, didecanoylphosphatidylcholine (DDPC), didodecanoylphosphatidylcholine, dierucoylphosphatidylcholine (DEPC), dilinoleoylphosphatidylcholine (DLOPC), dimyristoylphosphatidylcholine (DMPC), myristoylpalmitoylphosphatidylcholine (MPPC), myristoylstearoylphosphatidylcholine (MSPC), stearoylmyristoylphosphatidylcholine (SMPC), palmitoylmyristoylphosphatidylcholine (PMPC), palmitoylstearoylphosphatidylcholine (PSPC), stearoylpalmitoylphosphatidylcholine (SPPC), and stearoyloleoylphosphatidylcholine (SOPC), and mixtures thereof.

5. The nanoparticle of claim 3, wherein the diacylphospholipid is a phosphatidylcholine having a fatty acid component having from 10 to 22 carbons.

6. The nanoparticle of claim 3, wherein the diacylphospholipid is a phosphatidylcholine having a fatty acid component having from 10 to 12 carbons.

7. The nanoparticle of claim 1, wherein the one or more phospholipids is a mono-acylphospholipid selected from the group consisting of lysophosphatidylcholines, lysophosphatidylethanolamines, lysophosphatidylglycerols, lysophosphatidylserines, lysophosphatidylinositols, lysophosphatidic acids, and mixtures thereof.

8. The nanoparticle of claim 7, wherein the mono-acylphospholipid is a lysophosphatidylcholine having a fatty acid component having from 10 to 22 carbons.

9. The nanoparticle of claim 7, wherein the mono-acylphospholipid is a lysophosphatidylcholine having a fatty acid component having from 10 to 12 carbons.

10. The nanoparticle of claim 1, wherein the one or more phospholipids is a mixture of a mono-acylphospholipid and a diacylphospholipid.

11. The nanoparticle of claim 10, wherein the mono-acylphospholipid is a lysophosphatidylcholine having a fatty acid component having from 10 to 12 carbons, and the diacylphospholipid is a phosphatidylcholine having a fatty acid component having from 10 to 12 carbons.

12. The nanoparticle of claim 10, wherein the ratio of diacylphospholipid to mono-acylphospholipid is from about 90:10 to 60:40 w/w percent.

13. The nanoparticle of claim 10, wherein the ratio of diacylphospholipid to mono-acylphospholipid is about 80:20 w/w percent.

14. The nanoparticle of claim 1, wherein the therapeutic agent is therapeutic agent having an X log P greater than 2.0.

15. The nanoparticle of claim 1, wherein the therapeutic agent is selected from the group consisting of analgesics/antipyretics, anesthetics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antianginal agents, antipsychotic agents, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines/antipruritics, agents useful for calcium regulation, antibacterial agents, antiviral agents, antimicrobials, anti-infectives, bronchodialators, hormones, hypoglycemic agents, hypolipidemic agents, proteins, nucleic acids, agents useful for erythropoiesis stimulation, antiulcer/antireflux agents, antinauseants/antiemetics, and oil-soluble vitamins.

16. The nanoparticle of claim 1, wherein the therapeutic agent is an antineoplastic selected from adriamycin, cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, interferon, camptothecin and derivatives thereof, phenesterine, paclitaxel and derivatives thereof, docetaxel and derivatives thereof, epothilones and derivatives thereof, vinblastine, vincristine, tamoxifen, etoposide, or piposulfan.

17. The nanoparticle of claim 1, wherein the therapeutic agent is paclitaxel or derivatives thereof.

18. A pharmaceutical composition, comprising the nanoparticle of claim 1 and a pharmaceutically acceptable carrier.

19. The pharmaceutical composition of claim 18, wherein the nanoparticle is suspended in an aqueous medium.

20. The pharmaceutical composition of claim 19, wherein the composition further comprises a particle size stabilizing agent.

21. A method of treating a disease or condition in an individual treatable by administration of a therapeutic agent, comprising administering to an individual in need thereof a therapeutically effective amount of the nanoparticle of claim 1, wherein the nanoparticle comprises the therapeutic agent.

22. The method of claim 21, wherein the therapeutic agent is paclitaxel and the disease is a disease treatable by administering paclitaxel.

23. The method of claim 22, wherein the therapeutic agent is paclitaxel and the disease is a cancer treatable by administering paclitaxel.

24. A unit dosage form for treating in an individual, comprising the nanoparticle of claim 1 and a pharmaceutically acceptable carrier.

25. A kit, comprising a container comprising the nanoparticle of claim 1, a container comprising a pharmaceutically acceptable carrier for reconstituting the nanoparticle, and instructions for using the kit in treating a disease or condition.

26. A kit, comprising a container comprising the nanoparticle of claim 1 suspended in a pharmaceutically acceptable carrier, and instructions for using the kit in treating a disease or condition.

27. A pharmaceutical composition, comprising the nanoparticle of claim 2 and a pharmaceutically acceptable carrier.

28. A method of treating a disease or condition in an individual treatable by administration of a therapeutic agent, comprising administering to an individual in need thereof a therapeutically effective amount of the nanoparticle of claim 2, wherein the nanoparticle comprises the therapeutic agent.

29. A unit dosage form for treating in an individual, comprising the nanoparticle of claim 2 and a pharmaceutically acceptable carrier.

30. A kit, comprising a container comprising the nanoparticle of claim 2, a container comprising a pharmaceutically acceptable carrier for reconstituting the nanoparticle, and instructions for using the kit in treating a disease or condition.

* * * * *